United States Patent
Smith et al.

(10) Patent No.: US 12,065,636 B2
(45) Date of Patent: Aug. 20, 2024

(54) HIGH HYDROGEN UTILIZATION AND GAS RECYCLE

(71) Applicant: INV NYLON CHEMICALS AMERICAS, LLC, Wilmington, DE (US)

(72) Inventors: Gary J. Smith, North Yorkshire (GB); Paul S. Pearlman, Thornton, PA (US); Gregory S. Kirby, Avondale, PA (US)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 0 days.

(21) Appl. No.: 16/372,106

(22) Filed: Apr. 1, 2019

(65) Prior Publication Data

US 2019/0316072 A1 Oct. 17, 2019

Related U.S. Application Data

(60) Provisional application No. 62/650,590, filed on Mar. 30, 2018, provisional application No. 62/650,575, filed on Mar. 30, 2018.

(51) Int. Cl.
*C12M 1/00* (2006.01)
*C12M 1/34* (2006.01)
*C12P 7/625* (2022.01)

(52) U.S. Cl.
CPC .......... *C12M 29/24* (2013.01); *C12M 41/32* (2013.01); *C12M 41/34* (2013.01); *C12P 7/625* (2013.01)

(58) Field of Classification Search
CPC ...... C12M 29/24; C12M 41/34; C12M 43/02; C12P 7/625; C12P 1/00
See application file for complete search history.

(56) References Cited

U.S. PATENT DOCUMENTS

| | | | |
|---|---|---|---|
| 3,957,876 A | 5/1976 | Rapoport et al. | |
| 4,554,101 A | 11/1985 | Hopp | |
| 6,207,217 B1 | 3/2001 | Peoples et al. | |
| 6,888,034 B1 | 5/2005 | Landray et al. | |
| 7,384,783 B2 | 6/2008 | Kunas et al. | |
| 8,603,518 B2 | 12/2013 | Boon et al. | |
| 8,809,027 B1 | 8/2014 | Lynch et al. | |
| 8,986,960 B2 | 3/2015 | Sichwart | |
| 9,221,737 B2 | 12/2015 | Valdez | |
| 9,580,733 B2 | 2/2017 | Botes et al. | |
| 9,637,764 B2 | 5/2017 | Botes et al. | |
| 9,650,653 B2 | 5/2017 | Pearlman et al. | |
| 9,862,973 B2 | 1/2018 | Botes et al. | |
| 9,920,339 B2 | 3/2018 | Kadi et al. | |
| 10,072,150 B2 | 9/2018 | Conradie et al. | |
| 10,196,657 B2 | 2/2019 | Pearlman et al. | |
| 10,577,634 B2 | 3/2020 | Pearlman et al. | |
| 10,975,363 B2 | 4/2021 | Foster et al. | |
| 2002/0192786 A1 | 12/2002 | Yamada et al. | |
| 2005/0181499 A1 | 8/2005 | Brahmbhatt | |
| 2007/0264688 A1 | 11/2007 | Venter et al. | |
| 2007/0269862 A1 | 11/2007 | Glass et al. | |
| 2010/0120104 A1 | 5/2010 | Reed | |
| 2010/0167371 A1 | 7/2010 | Chotani et al. | |
| 2011/0125118 A1 | 5/2011 | Lynch | |
| 2011/0171702 A1 | 7/2011 | Reinecke et al. | |
| 2012/0003706 A1* | 1/2012 | Hickey | C12P 7/04 435/141 |
| 2012/0064622 A1 | 3/2012 | Fischer et al. | |
| 2012/0295334 A1 | 11/2012 | Brahmbhatt | |
| 2013/0034884 A1 | 2/2013 | Burgard et al. | |
| 2013/0065285 A1* | 3/2013 | Sefton | C12M 29/06 435/135 |
| 2013/0177957 A1 | 7/2013 | Du et al. | |
| 2013/0189763 A1* | 7/2013 | Dalla-Betta | C12N 1/20 435/286.1 |
| 2013/0323714 A1 | 12/2013 | Cheng et al. | |
| 2014/0248687 A1 | 9/2014 | Kelly et al. | |
| 2014/0330398 A1 | 11/2014 | Fan et al. | |
| 2015/0132815 A1* | 5/2015 | Hickey | C12P 7/06 435/141 |
| 2015/0315599 A1 | 11/2015 | Shetty et al. | |
| 2016/0176813 A1 | 6/2016 | Valdez | |
| 2017/0107474 A1 | 4/2017 | Farmer et al. | |
| 2017/0159082 A1 | 6/2017 | Conradie et al. | |

(Continued)

FOREIGN PATENT DOCUMENTS

| | | |
|---|---|---|
| CN | 1735691 A | 2/2006 |
| CN | 102459579 A | 5/2012 |

(Continued)

OTHER PUBLICATIONS

Tanaka et al., Biotechnology and Bioengineering, vol. 45, No. 3, pp. 268-275; 1995 (of record). (Year: 1995).*
"Cupriavidus necator", Wikipedia, Retrieved from Internet URL: https://en.wikipedia.org/wiki/Cupriavidus_necator, Feb. 25, 2021, 7 Pages.
Tanaka et al., "Production of Poly(D-3-Hydroxybutyrate) from C02, H2, and 02 by High Cell Density Autotrophic7 Cultivation of Alcaligenes Eutrophus", Biotechnology and Bioengineering, vol. 45, No. 3, Feb. 5, 1995, pp. 268-275.
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue 4, 1994, pp. 425-427.
Zeph, et al., "Gram-Negative Versus Gram-Positive (Actinomycete) Nonobligate Bacterial Predators of Bacteria in Soil", Applied Environmental Microbiology, vol. 52, No. 4 Oct. 1986, pp. 819-823.

(Continued)

*Primary Examiner* — Jeanette M Lieb
*Assistant Examiner* — Paul C Martin

(57) ABSTRACT

Provided herein are systems and methods for recycling and supplementing off-gas from a gas fed reaction process. The systems and methods are particularly useful for bioprocesses that convert hydrogen gas into one or more biosynthetic products. By maintaining separate hydrogen and oxygen feed gas streams, and forming a recycle gas that introduces a target component of the supply gas to the bioreactor within a target concentration range, the yields, productivities, and safety profiles of the bioprocess can be enhanced.

20 Claims, 4 Drawing Sheets

(56) References Cited

U.S. PATENT DOCUMENTS

| | | |
|---|---|---|
| 2017/0218406 A1 | 8/2017 | Conradie et al. |
| 2018/0023088 A1 | 1/2018 | Van Eck Conradie et al. |
| 2018/0023103 A1 | 1/2018 | Foster et al. |
| 2018/0023104 A1 | 1/2018 | Cartman et al. |
| 2018/0100160 A1 | 4/2018 | Bawdon et al. |
| 2018/0327705 A1 | 11/2018 | Matsuka et al. |
| 2019/0124947 A1 | 5/2019 | Pearlman et al. |
| 2019/0300839 A1 | 10/2019 | Smith et al. |
| 2019/0316072 A1 | 10/2019 | Smith et al. |
| 2019/0338320 A1 | 11/2019 | Foster et al. |
| 2019/0352674 A1 | 11/2019 | Foster et al. |
| 2019/0352682 A1 | 11/2019 | Foster et al. |
| 2019/0359957 A1 | 11/2019 | Foster et al. |

FOREIGN PATENT DOCUMENTS

| | | |
|---|---|---|
| CN | 106795537 A | 5/2017 |
| CN | 107849300 A | 3/2018 |
| EP | 995490 A2 | 4/2000 |
| EP | 1728853 A1 | 12/2006 |
| EP | 1938892 A1 | 7/2008 |
| EP | 3399015 | 11/2018 |
| JP | S49124358 A | 11/1974 |
| JP | H03127983 A | 5/1991 |
| JP | 2007185133 A | 7/2007 |
| JP | 2009225662 A | 10/2009 |
| JP | 2013179909 A | 9/2013 |
| RU | 2644344 C1 | 2/2018 |
| WO | 2008094282 A1 | 8/2008 |
| WO | 2010003007 A2 | 1/2010 |
| WO | 2010069313 A1 | 6/2010 |
| WO | 2013090769 A2 | 6/2013 |
| WO | 2013186340 | 12/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2015032375 A1 | 3/2015 |
| WO | 2015117019 A1 | 8/2015 |
| WO | 2015149147 A1 | 10/2015 |
| WO | 2015195654 A1 | 12/2015 |
| WO | 2017115855 A1 | 7/2017 |
| WO | 2017165244 | 9/2017 |
| WO | 2017165244 A1 | 9/2017 |
| WO | 2018005770 A2 | 1/2018 |
| WO | 2018022595 A1 | 2/2018 |
| WO | 2018022633 A1 | 2/2018 |
| WO | 2018106549 A1 | 6/2018 |
| WO | 2013152051 A2 | 10/2019 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |
| WO | 2019213108 A1 | 11/2019 |
| WO | 2019213118 A1 | 11/2019 |

OTHER PUBLICATIONS

Abayomi, Oluwanbe Johnson., et al., "An engineered constitutive promoter set with broad activity range for Cupriavidus necator H16", Acs Synthetic Biology, vol. 7, (Jun. 27, 2018), XP002792846, Jun. 27, 2018, pp. 1918-1928.

Atlic, et al., "Continuous Production of Poly([R]-3-Hydroxybutyrate) by Cupriavidus Necator in a Multistage Bioreactor Cascade", Applied Microbialgy and Biotechnology, vol. 91, 2011, pp. 295-304.

Brigham, C.J., et al., "Engineering Ralstonia eutropha for Production of Isobutanol from C02, H2 and O2", Advanced Biofuels and Bioproducts, (2013) Chapter 39, pp. 1065-1090.

Byrd, et al. "Bacterial Control of Agromyces Ramosus in Soil Canadian Journal of Microbiology", vol. 31, No. 12, 1985, pp. 1157-1163.

Chae, Tong Un., et al., Metabolic engineering of *Escherichia coli* for the production of four-, five- and six-carbon lactams Metabolic Engineering, Academic Press, Us, vol. 41 Apr. 5, 2017 82-91.

Chi, Nguyen, et al., "Trapping the dynamic acyl carrier protein in fatty acid biosynthesis", Nature, vol. 505, No. 7483, Dec. 22, 2013, pp. 427-431.

Eggers, et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24, Dec. 2014, pp. 7702-7709.

Feng, Yanbin, et al., "Tuning of acyl-ACP thioesterase activity directed for tailored fatty acid synthesis Applied Microbiology And Biotechnology", Springer, De, vol. 102, No. 7, Feb. 22, 2018, pp. 3173-3182.

Fernando, Silva, et al., "Impact of nitrogen feeding regulation on polyhydroxyalkanoates production by mixed microbial cultures", New Biotechnology, vol. 37, XP029943712 2017, pp. 90-98.

Gabriela, Montiel-Jarillo, et al., "Enrichment of a mixed microbial culture for polyhydroxyalkanoates production: Effect of pH and N and P concentrations", Science Of The Total Environment, vol. 583, XP029914697, 2017, pp. 300-307.

Girdhar, Amandeep, et al., "Process Parameters for Influencing Polyhydroxyalkanoate Producing Bacterial Factories: An Overview", Journal of Petroleum & Environmental Biotechnology, vol. 4, No. 5, 2013, p. 8.

Hanko, Erik K. R.., et al., "Characterisation of a 3-hydroxypropionic acid-inducible system from Pseudomonas putida for orthogonal gene expression control in *Escherichia coli* and Cupriavidus necator", Scientific Reports, vol. 7, XP002792878, 2017, pp. 1-12.

Horvat, et al., "Mathematical Modelling and Process Optimization of a Continuous 5-Stage Bioreactor Cascade for Production of Poly[-(R)-3-Hydroxybutyrate] by Cupriavidus Necator", Bioprocess Biosyst Eng, vol. 36, 2013, pp. 1235-1250.

Hun-Suk, Song, et al. "Enhanced isobutanol production from acetate by combinatorial overexpression of acetyl-CoA synthetase and anaplerotic enzymes in engineered *Escherichia coli*", Biotechnology And Bioengineering, vol. 115, (May 2, 2018), XP002792879, May 2, 2018, pp. 1971-1978.

International Application No. PCT/US2019/025194, "Invitation to Pay Additional Fees and, Where Applicable, Protest Fee", dated Jul. 1, 2019, 15 pages.

International Search Report and Written Opinion for International Application No. PCT/US2019/025202, dated Jul. 30, 2019, 13 pages.

International Search Report and Written Opinion for International Application Serial No. PCT/US2019/025194, dated Aug. 22, 2019, pp. 8.

International Search Report and Written Opinion for International Application Serial No. PCT/US2019/025211, dated Jul. 29, 2019, pp. 9.

International Search Report and Written Opinion for International Application Serial No. PCT/US2019/025218, dated Sep. 5, 2019, pp. 17.

International Search Report and Written Opinion for International Application Serial No. PCT/US2019/029956, dated Aug. 13, 2019, pp. 6.

International Search Report and Written Opinion for International Application Serial No. PCT/US2019/029973, dated Jul. 23, 2019, pp. 5.

Ishizaki, A., et al., "Microbial production of poly-D-3-hydroxybutyrate from CO2", Applied Microbiology and Biotechnology, vol. 57, Oct. 2001, pp. 6-12.

Janina, Kluge, et al. "Inducible promoters and functional genomic approaches for the genetic engineering of filamentous fungi", Applied Microbiology And Biotechnology, vol. 102, (Jun. 2, 2018), XP036546152, Jun. 2, 2018, pp. 6357-6372.

Jayashree, Chakravarty, et al., "Solvent production by engineered Ralstonia eutropha: channeling carbon to biofuel", Applied Microbiology And Biotechnology, vol. 102, (Apr. 29, 2018), XP036507417, early online publication Apr. 29, 2018 5021-5031.

Jiachao, Zhu, et al., "Factors for promoting polyhydroxyalkanoate (PHA) synthesis in bio-nutrient-removal and recovery system" 4th International Conference on Environmental Systems Research (ICESR

(56) References Cited

OTHER PUBLICATIONS

2017) Conference paper, XP002792821, DOI: 10.1088/1755-1315/178/1/012021, cited as a P-document, but the conference was held in 2017, 2018, pp. 1-4.

Jillian, Marc, et al., "Over expression of GroESL in Cupriavidus necator for heterotrophic and autotrophic isopropanol production", Metabolic Engineering, vol. 42, XP085136193 2017, pp. 74-84.

Jones, G.W. and Kennedy, R.E., "Prevention of Gas Explosions by Controlling Oxygen Concentration", Industrial and Engineering Chemistry, vol. 27, Issue 11, 1935, pp. 1344-1346.

Joris, Beld, et al., Evolution of acyl-ACP thioesterases and [beta]-ketoacyl-ACP synthases revealed by protein-protein Interactions Journal Of Applied Phycology., vol. 26, No. 4 Nov. 22, 2013 1619-1629.

Judger, B-E., et al., "An analysis of the changes in soluble hydrogenase and global gene expression in Cupriavidus necator (Ralstonia eutropha) HI6 grown in heterotrophic diauxic batch culture", Microbial Cell Factories, vol. 14, 2015, pp. 1-11.

Justyna, Mozejko-Ciesielska, et al., "Bacterial polyhydroxyalkanoates: Still fabulous ?", Microbiological Research, vol. 192, XP029740446, and reference Horng 2016, pp. 271-282.

Katalin, Kovacs, et al. Metabolic engineering of Cupriavidus necator H16 for the sustainable production of C3 and C5 monomers and polymers Clnet Conference 4, Conference paper (Abstract), 2019, XP002792880, The oral disclosure may have been more important (?); the publication date is presumably, Jan. 2019, 26 pgs.

Kianoush, Khosravi-Darani, et al., Simulation of bioreactors for poly(3-hydroxybutyrate) production from natural gas Iranian Journal Of Chemistry And Chemical Engineering, vol. 39, XP002792822, (Modeling of . . . ); online publication in late 2018, pp. 1-24.

Klasson, K.T., et al., "Bioreactor design for synthesis gas fermentations", Fuel , vol. 70, Issue 5, 1991, pp. 605-614.

Koller, et al., "Potential and Prospects of Continuous Polyhydroxyalkanoate (PHA)", Production Bioengineering, May 29, 2015, pp. 94-121.

Koller, M., "A review on established and emerging fermentation schemes for microbial production of polyhydroxyalkanoate (PHA) biopolyesters", Fermentation, vol. 4, (Apr. 23, 2018), XP002792757, early online publication Apr. 23, 2018, pp. 1-30.

Kunasundari, et al., "Revisiting the Single Cell Protein Application of Cupriavidus Necator H16 and Recovering Bioplastic Granules Simultaneously", Plos One, vol. 8, No. 10 Oct. 2013, 15 pgs.

Maddipati, P., "Ethanol production from syngas by Clostridium strain P11 using corn steep liquor as a nutrient replacement to yeast extract", Bioresoure Technology, vol. 102, Issue 11, 2011, pp. 6494-6501.

Makkar, et al., "*Cupriavidus Necator* Gen. *Nov.,* Sp. *Nov.:* A Nonobligate Bacterial Predator of Bacteria in Soil", International Journal of Systematic Bacteriology, vol. 37, No. 4, Oct. 1987, pp. 323-326.

Marika, Zlesack, et al., "Chimeric Fatty Acyl-Acyl Carrier Protein Thioesterases Provide Mechanistic Insight into Enzyme Specificity and Expression", Applied And Environmental Microbiology, vol. 84, No. 10, Mar. 16, 2018, pp. 12.

Martin, Koller, et al., "Continuous production mode as a viable process-engineering tool for efficient poly (hydroxyalkanoate) (PHA) bio-production", Chemical And Biochemical Engineering Quarterly, vol. 28, XP002792820, 2014, pp. 65-77.

Matthias, Raberg, et al., "Ralstonia eutropha H16 in progress: applications beside PHAs and establishment as production platform by advanced genetic tools", Critical Reviews In Biotechnology, vol. 38, (Dec. 12, 2017), XP002792845, early online publication Dec. 12, 2017, pp. 494-510.

Miglena, Manandhar, et al., "Pimelic acid, the first precursor of the Bacillus subtilis biotin synthesis pathway, exists as the free acid and is assembled by fatty acid synthesis", Molecular Microbiology, vol. 104, No. 4, Mar. 3, 2017, pp. 595-607.

Phillips, J.R., et al., "Syngas Fermentation: A Microbial Conversion Process of Gaseous Substrates to Various Products", Fermentation, vol. 3, Issue 2, 2017, pp. 26.

Raberg, et al., "A Closer Look on the Polyhydroxybutyrate- (PHB-) Negative Phenotype of Ralstonia Eutropha PHB-4", Plos One, vol. 9, No. 5, May 2014, pp. 1-11.

Robert, Haushalter W., et al., "Production of Odd-Carbon Dicarboxylic Acids in *Escherichia coli* Using an Engineered Biotin-Fatty Acid Biosynthetic Pathway", Journal Of The American Chemical Society, vol. 139, No. 13, Mar. 21, 2017, pp. 4615-4618.

Russell, J.B., "The Energy Spilling Reactions of Bacteria and Other Organisms", Journal of Molecular Microbiology Biotechnology, vol. 13, No. 1, 2007, pp. 1-11.

Shively, J.M. et al., "Something From Almost Nothing: Carbon Dioxide Fixation in Chemoautotrophs", Annual Review of Microbiology, vol. 52, 1998, pp. 191-230.

Sillman, et al., Isolation of Nonobligate Bacterial Predators of Bacteria from Soil Canadian Journal of Microbiology, vol. 32, No. 9, 1986, pp. 760-762.

Swathi, Alagesan, et al., "Functional genetic elements for controlling gene expression in Cupriavidus necator H16", Applied And Environmental Microbiology, vol. 84, (Oct. 2018), XP055604488, Oct. 2018, pp. 1-17.

"Aspartate aminotransferase family protein [Chromobacterium phragmitis]", NCBI Reference Sequence: WP_114062556.1, Dec. 20, 2020, 1 page.

"Aeration" available at https://www.clrblu.com/aeration/, (Year: 2021), 2 pages.

"Aminotransferase class III-fold pyridoxal phosphate-dependent enzyme [Aquitalea denitrificans]", NCBI Reference Sequence: WP_159877958.1, Jan. 19, 2020, 1 page.

"Aminotransferase class III-fold pyridoxal phosphate-dependent enzyme [Aquitalea sp. LB_tupeE]", NCBI Reference Sequence: WP_178973970.1, Jul. 11, 2020, 1 page.

"Aminotransferase class III-fold pyridoxal phosphate-dependent enzyme [Chromobacterium haemolyticum]", NCBI Reference Sequence: WP_166453011.1, Apr. 6, 2020, 1 page.

"Aminotransferase class III-fold pyridoxal phosphate-dependent enzyme [Chromobacterium vaccinii]", NCBI Reference Sequence: WP_166440807.1, Apr. 6, 2020, 1 page.

"Aminotransferase class III-fold pyridoxal phosphate-dependent enzyme [Crenobacter sedimenti]", NCBI Reference Sequence: WP_163315775.1, Apr. 6, 2020, 1 page.

"Aminotransferase class III-fold pyridoxal phosphate-dependent enzyme [Neisseriaceae bacterium B2N2-7]", GenBank: MXR37125.1, Jan. 6, 2020, 2 pages.

"Aminotransferase class III-fold pyridoxal phosphate-dependent enzyme [Paludibacterium paludis]", NCBI Reference Sequence: WP_189532963.1, Sep. 28, 2020, 1 page.

"Aminotransferase class III-fold pyridoxal phosphate-dependent enzyme [Paludibacterium sp. dN 18-1]", GenBank: MTD33855.1, Nov. 24, 2019, 1 page.

"Aminotransferase class III-fold pyridoxal phosphate-dependent enzyme [Vogesella alkaliphila]", NCBI Reference Sequence: WP_189374996.1, Sep. 28, 2020, 1 page.

"Aminotransferase class III-fold pyridoxal phosphate-dependent enzyme [Vogesella fluminis]", NCBI Reference Sequence: WP_189352298.1, Sep. 28, 2020, 1 page.

"Aminotransferase class III-fold pyridoxal phosphate-dependent enzyme [Vogesella oryzae]", NCBI Reference Sequence: WP_174874069.1, Jun. 22, 2020, 1 page.

"Aspartate aminotransferase family protein [Aquitalea magnusonii]", NCBI Reference Sequence: WP_059287319.1, Dec. 31, 2020. 1 page.

"Aspartate aminotransferase family protein [Aquitalea magnusonii]", NCBI Reference Sequence: WP_089085350.1, Jul. 15, 2017, 1 page.

"Aspartate aminotransferase family protein [Aquitalea sp. FJL05]", NCBI Reference Sequence: WP_124643387.1, Apr. 12, 2019, 1 page.

"Aspartate aminotransferase family protein [Aquitalea sp. THG-DN7.12]", NCBI Reference Sequence: WP_137009623.1, Oct. 16, 2019, 1 page.

"Aspartate aminotransferase family protein [Chromobacterium amazonense]", NCBI Reference Sequence: WP_106076402.1, Mar. 16, 2018, 1 page.

(56) References Cited

OTHER PUBLICATIONS

"Aspartate aminotransferase family protein [Chromobacterium haemolyticum]", GenBank: OQS32233.1, Apr. 6, 2017, 2 pages.
"Aspartate aminotransferase family protein [Chromobacterium haemolyticum]", GenBank: OQS37730.1, Apr. 6, 2017, 2 pages.
"Aspartate aminotransferase family protein [Chromobacterium haemolyticum]", NCBI Reference Sequence: WP_043593957.1, Apr. 15, 2016, 1 page.
"Aspartate aminotransferase family protein [Chromobacterium haemolyticum]", NCBI Reference Sequence: WP_081556739.1, Apr. 8, 2017, 1 page.
"Aspartate aminotransferase family protein [Chromobacterium haemolyticum]", NCBI Reference Sequence: WP_081576047.1, Apr. 8, 2017, 1 page.
"Aspartate aminotransferase family protein [Chromobacterium haemolyticum]", NCBI Reference Sequence: WP_161523523.1, Oct. 5, 2020, 1 page.
"Aspartate aminotransferase family protein [Chromobacterium paludis]", NCBI Reference Sequence: WP_149295777.1, Oct. 5, 2020, 1 page.
"Aspartate aminotransferase family protein [Chromobacterium sp. ATCC 53434]", NCBI Reference Sequence: WP_101708025.1, Jan. 10, 2018.
"Aspartate aminotransferase family protein [Chromobacterium sp. LK11]", NCBI Reference Sequence: WP_048412320.1, Apr. 15, 2016, 1 page.
"Aspartate aminotransferase family protein [Chromobacterium sp. LK1]", NCBI Reference Sequence: WP_048411976.1, Apr. 15, 2016, 1 page.
"Aspartate aminotransferase family protein [Chromobacterium sp. MWU13-2610]", NCBI Reference Sequence: WP_103321487.1, Jan. 31, 2018, 1 page.
"Aspartate aminotransferase family protein [Chromobacterium sp. MWU14-2602]", NCBI Reference Sequence: WP_103903523.1, Feb. 10, 2018, 1 page.
"Aspartate aminotransferase family protein [Chromobacterium sp. Panama]", NCBI Reference Sequence: WP_107799474.1, Apr. 25, 2018, 1 page.
"Aspartate aminotransferase family protein [Chromobacterium sphagni]", NCBI Reference Sequence: WP_071116856.1, Aug. 23, 2017, 1 page.
"Aspartate aminotransferase family protein [Chromobacterium subtsugae]", NCBI Reference Sequence: WP_047237256.1, Mar. 20, 2018, 1 page.
"Aspartate aminotransferase family protein [Chromobacterium subtsugae]", NCBI Reference Sequence: WP_047243213.1, Apr. 15, 2016, 1 page.
"Aspartate aminotransferase family protein [Chromobacterium subtsugae]", NCBI Reference Sequence: WP_047257673.1, Apr. 15, 2016, 1 page.
"Aspartate aminotransferase family protein [Chromobacterium vaccinii]", NCBI Reference Sequence: WP_046156378.1, Oct. 25, 2019, 1 page.
"Aspartate aminotransferase family protein [Chromobacterium vaccinii]", NCBI Reference Sequence: WP_104946997.1, Mar. 4, 2018, 1 page.
"Aspartate aminotransferase family protein [Chromobacterium violaceum]", NCBI Reference Sequence: WP_011135573.1, Jul. 28, 2019, 1 page.
"Aspartate aminotransferase family protein [Chromobacterium violaceum]", NCBI Reference Sequence: WP_048405256.1, Apr. 15, 2016, 1 page.
"Aspartate aminotransferase family protein [Chromobacterium violaceum]", NCBI Reference Sequence: WP_081573061.1, Apr. 8, 2017, 1 page.
"Aspartate aminotransferase family protein [Chromobacterium violaceum]", NCBI Reference Sequence: WP_152637556.1, Oct. 31, 2019, 1 page.
"Aspartate aminotransferase family protein [Crenobacter sp. GY 70310]", NCBI Reference Sequence: WP_136552942.1, Oct. 16, 2019, 1 page.
"Aspartate aminotransferase family protein [Gulbenkiania indica]", NCBI Reference Sequence: WP_055434103.1, May 14, 2017, 1 page.
"Aspartate aminotransferase family protein [Gulbenkiania mobilis]", NCBI Reference Sequence: WP_054286466.1, May 14, 2017, 1 page.
"Aspartate aminotransferase family protein [Paludibacterium purpuratum]", NCBI Reference Sequence: WP_133682408.1, May 12, 2019, 1 page.
"Aspartate aminotransferase family protein [Paludibacterium yongneupense]", NCBI Reference Sequence: WP_028535161.1, Apr. 15, 2016, 2 pages.
"Aspartate aminotransferase family protein [Pseudogulbenkiania ferrooxidans]", NCBI Reference Sequence: WP_008952788.1, Apr. 15, 2016, 2 pages.
"Aspartate aminotransferase family protein [Pseudogulbenkiania ferrooxidans]", NCBI Reference Sequence: WP_021478068.1, Apr. 15, 2016, 1 page.
"Aspartate aminotransferase family protein [Pseudogulbenkiania sp. MAI-1]", NCBI Reference Sequence: WP_024302818.1, Apr. 15, 2016, 2 pages.
"Aspartate aminotransferase family protein [*Pseudogulbenkiania* sp. NH8B]", NCBI Reference Sequence: WP_014087389.1, Apr. 15, 2016, 2 pages.
"Aspartate aminotransferase family protein [Pseudogulbenkiania subflava]", NCBI Reference Sequence: WP_085275708.1, Apr. 22, 2017, 1 page.
ꝋAspartate aminotransferase family protein [Vogesella indigofera]⇋, NCBI Reference Sequence: WP_120809711.1, Nov. 4, 2018, 1 page.
"Aspartate aminotransferase family protein [Vogesella mureinivorans]", NCBI Reference Sequence: WP_147694092.1, Oct. 5, 2020, 1 page.
"Aspartate aminotransferase family protein [Vogesella perlucida]", NCBI Reference Sequence: WP_147687830.1, Oct. 5, 2020, 1 page.
"Aspartate aminotransferase family protein [*Vogesella* sp. EB]", NCBI Reference Sequence: WP_047966302.1, Apr. 15, 2016, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [Vogesella urethralis]", NCBI Reference Sequence: WP_144371715.1, Oct. 5, 2020, 1 page.
"Aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB: 6S4G_A, Dec. 1, 2020, 2 pages.
"Multispecies: aspartate aminotransferase family protein [Aquitalea]", NCBI Reference Sequence: WP_045848621.1, Apr. 15, 2016, 1 page.
"Multispecies: aspartate aminotransferase family protein [Aquitalea]", NCBI Reference Sequence: WP_103523625.1, Aug. 6, 2020, 1 page.
"Multispecies: aspartate aminotransferase family protein [Chromobacterium]", NCBI Reference Sequence: WP_019104435.1, Apr. 18, 2017, 1 page.
"Multispecies: aspartate aminotransferase family protein [Chromobacterium]", NCBI Reference Sequence: WP_043572477.1, Apr. 15, 2016, 1 page.
"Multispecies: aspartate aminotransferase family protein [Chromobacterium]", NCBI Reference Sequence: WP_043629242.1, Oct. 31, 2016, 1 page.
"Multispecies: aspartate aminotransferase family protein [Chromobacterium]", WP_043638691.1, Nov. 11, 2020, 1 page.
"Multispecies: aspartate aminotransferase family protein [Microvirgula]", NCBI Reference Sequence: WP_028498438.1, Jul. 14, 2018, 1 page.
"TPA: aspartate aminotransferase family protein [Betaproteobacteria bacterium]", GenBank: HEL32111.1, Mar. 2, 2020, 1 page.
Alagesan, S, et al., "13C-assisted metabolic flux analysis to investigate heterotrophic and mixotrophic metabolism in Cupriavidus necator H16", Metabolomics, vol. 14, Issue 9, 2018, 9 pgs.

(56) References Cited

OTHER PUBLICATIONS

Anderson, A. J.., et al., "Occurrence, Metabolism, Metabolic Role, and Industrial Uses of Bacterial Polyhydroxyalkanoates", Microbiological Review, 54(4), 1990, pp. 450-472.
U.S. Appl. No. 16/372,072, Corrected Notice of Allowability dated Jan. 26, 2021, 2 pages.
U.S. Appl. No. 16/372,072, Non Final Office Action dated Mar. 6, 2020, 20 pages.
U.S. Appl. No. 16/372,072, Notice of Allowance dated Jul. 17, 2020, 11 pages.
U.S. Appl. No. 16/372,072, Notice of Allowance dated Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement dated Dec. 11, 2019, 7 pages.
U.S. Appl. No. 16/372,072, Response filed Jun. 8, 2020 to Non Final Office Action dated Mar. 6, 2020, 11 pages.
U.S. Appl. No. 16/372,072, Restriction Requirement dated Dec. 11, 2019, 9 pages.
U.S. Appl. No. 16/372,083, Non Final Office Action dated Apr. 27, 2021, 14 pages.
U.S. Appl. No. 16/372,083, Preliminary Amendment filed Jul. 30, 2019, 4 pages.
U.S. Appl. No. 16/372,083, Response filed Apr. 12, 2021 to Restriction Requirement dated Mar. 8, 2021, 8 pages.
U.S. Appl. No. 16/372,083, Response filed Dec. 18, 2020 to Restriction Requirement dated Oct. 19, 2020, 7 pages.
U.S. Appl. No. 16/372,083, Restriction Requirement dated Mar. 8, 2021, 6 pages.
U.S. Appl. No. 16/372,083, Restriction Requirement dated Oct. 19, 2020, 8 pages.
U.S. Appl. No. 16/372,092, Final Office Action dated Jul. 26, 2021, 10 pages.
U.S. Appl. No. 16/372,092, Non Final Office Action dated Mar. 4, 2021, 9 pages.
U.S. Appl. No. 16/372,092, Response filed Jun. 2, 2021 to Non Final Office Action dated Mar. 4, 2021, 11 pgs.
U.S. Appl. No. 16/372,092, Response filed Dec. 17, 2020 to Restriction Requirement dated Oct. 21, 2020, 6 pages.
U.S. Appl. No. 16/372,092, Restriction Requirement dated Oct. 21, 2020, 7 pages.
U.S. Appl. No. 16/372,099, Non Final Office Action dated Jul. 9, 2021, 14 pages.
U.S. Appl. No. 16/372,099, Response filed May 18, 2021 to Restriction Requirement dated Mar. 19, 2021, 6 pages.
U.S. Appl. No. 16/372,099, Restriction Requirement dated Mar. 19, 2021, 6 pages.
U.S. Appl. No. 16/398,351, Non Final Office Action dated Feb. 1, 2021, 24 pages.
U.S. Appl. No. 16/398,365, Non Final Office Action dated Jan. 25, 2021, 10 pages.
U.S. Appl. No. 16/398,384, Non Final Office Action dated Oct. 23, 2020, 13 pages.
U.S. Appl. No. 16/398,401, Non Final Office Action dated Feb. 16, 2021, 29 pages.
U.S. Appl. No. 16/399,145, Advisory Action dated Feb. 1, 2021, 4 pages.
U.S. Appl. No. 16/399,145, Final Office Action dated Dec. 4, 2020, 17 pages.
U.S. Appl. No. 16/399,145, Non Final Office Action dated Jun. 17, 2021, 20 pages.
U.S. Appl. No. 16/399,145, Non Final Office Action dated Aug. 12, 2020, 16 pages.
U.S. Appl. No. 16/399,145, Response filed Jan. 25, 2021 to Final Office Action dated Dec. 4, 2020, 12 pages.
U.S. Appl. No. 16/399,145, Response filed Jun. 3, 2020 to Restriction Requirement dated Apr. 17, 2020, 7 pages.
U.S. Appl. No. 16/399,145, Response filed Nov. 6, 2020 to Non Final Office Action dated Aug. 12, 2020, 12 pages.
U.S. Appl. No. 16/399,145, Restriction Requirement dated Apr. 17, 2020, 9 pages.
U.S. Appl. No. 16/399,155, Advisory Action dated Jun. 1, 2020, 3 pages.
U.S. Appl. No. 16/399,155, Final Office Action dated Mar. 5, 2020, 23 pages.
U.S. Appl. No. 16/399,155, Non Final Office Action dated Feb. 16, 2021, 17 pages.
U.S. Appl. No. 16/399,155, Response filed May 5, 20 to Final Office Action dated Mar. 5, 2020, 12 pages.
U.S. Appl. No. 16/399,155, Response filed May 14, 2021 to Non Final Office Action dated Feb. 16, 2021, 11 pages.
U.S. Appl. No. 16/399,155, Response filed Jun. 5, 2020 to Advisory Action dated Jun. 1, 2020, 13 pages.
U.S. Appl. No. 16/399,155, Response filed Jun. 5, 2020 to Final Office Action dated Mar. 5, 2020, 13 pages.
Bramer, C O., "The malate dehydrogenase of Ralstonia eutropha and functionality of the C(3)/C(4) metabolism in a Tn5-induced mdh mutant", FEMS Microbiol Letters, vol. 212, Issue 2, Jul. 2, 2002, pp. 159-164.
Brandt, U, et al., "Elevated poly(3-hydroxybutyrate) synthesis in mutants of Ralstonia eutropha H16 defective in popolysaccharide biosynthesis", Applied Microbiology and Biotechnology, 2012, vol. 95, 2012, pp. 471-483.
Brigham, C J., et al., "Correction for Whole-genome microarray and gene deletion studies reveal regulation of the polyhydroxyalkanoate production cycle by the stringent response in Ralstonia eutropha H16", Appl Environ Microbiol., vol. 83, Issue 15, 2017, pp. 1-2.
Brigham, C J., et al., "Whole-genome microarray and gene deletion studies reveal regulation of the polyhydroxyalkanoate production cycle by the stringent response in Ralstonia eutropha HI6", Appl Environ Microbial., vol. 78, Issue 22, 2012, pp. 8033-8044.
Brown, D R., et al., "Nitrogen stress response and stringent response are coupled in *Escherichia coli*", Nature communications, 2014, vol. 5, 4115, , 8 pgs.
Bruland, et al., "Unravelling the C3/C4 carbon metabolism in Ralstonia eutropha H16", Journal of Applied Microbiology, 109, 2010, pp. 79-90.
Chen, R, et al., "A highly active decarboxylating dehydrogenase with rationally inverted coenzyme specificity", PNAS, vol. 92, Issue 25, 1996, pp. 11666-11670.
Chen, R, et al., "Redesigning secondary structure to invert coenzyme specificity in isopropylmalate dehyrogenase", PNAS, vol. 93, 1996, pp. 12171-12176.
Choi, J C., et al., "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbial Technology, vol. 32, Issue 1, 2003, pp. 178-185 (Abstract Only).
Cramm, R. J., "Genomic view of energy metabolism in Ralstonia eutropha HI6", Journal of Molecular Microbiology and Biotechnology, vol. 16, 2009, pp. 38-52.
Deveraux, J., et al., "A comprehensive set of sequence analysis programs for the VAX", Nucleic Acids Research, 12 (1 Part 1), 1984, pp. 387-395.
Devos, et al., "Practical limits of function prediction", Proteins: Structure, Function, and Genetics vol. 41, 2000, pp. 98-107.
Ding, H, et al., "Glycerol utilization by Rhizobium leguminosarum requires an ABC transporter and affects competition for nodulation", Microbiology, vol. 158, 2012, pp. 1369-1378.
Doberstein, C., et al., "Polythioester synthesis in Ralstonia eutropha H16: novel insights into 3,3'-thiodipropionic acid and 3,3'-dithiodipropionic acid catabolism", Journal of Biotechnology, vol. 184, 2014, pp. 187-198 (Abstract Only).
Du, et al., "Effects of Environmental Conditions on Cell Growth and Poly-β-Hydroxybutyrate Accumulation in Alcaligenes Eutrophus", World Journal of Microbiology & Biotechnology, vol. 16, 2000, pp. 9-13.
Gao, C, et al., "Lactate utilization is regulated by the FadR-type regulator LidR in Pseudomonas aeruginosa", Journal of Bacteriology, vol. 194, 2012, pp. 2687-2692.

(56) References Cited

OTHER PUBLICATIONS

Grousseau, et al., "Isopropanol Production with Engineered Cupriavidus Necator as Bioproduction Platform", Appl. Microbial. Biotechnol., vol. 98, No. 9, 2014, pp. 4277-4290.
Gyaneshwar, et al., "Sulfur and Nitrogen Limitation in *Escherichia coli* K-12: Specific Homeostatic Responses", Journal of Bacteriology, vol. 187, No. 3, Feb. 2005, pp. 1074-1090.
Hauryliuk, V, et al., "Recent functional insights into the role of (p)ppGpp in bacterial physiology", Nature Reviews Microbiology, vol. 13, 2015, pp. 298-309.
Hensirisak, P., et al., "Scale-Up of Microbubble Dispersion Generator for Aerobic Fermentation", Applied Biochemistry and Biotechnology, vol. 101, 2002, p. 211-227 (Year: 2002).
Inoue, H, et al., "Biochemical and molecular characterization of the NAD(+)-dependent isocitrate dehydrogenase from the chemolithotrophAcidithiobacillus thiooxidans", FEMS Microbial Letters, vol. 214, Issue 1, 2002, pp. 127-132.
International Application Seria No. PCT/US2019/029795, Written Opinion dated Jul. 11, 2019, 6 pages.
International Application Serial No. PCT/US2019/025189, International Preliminary Report on Patentability dated Oct. 15, 2020, 9 pages.
International Application Serial No. PCT/US2019/025194, International Preliminary Report on Patentability dated Oct. 15, 2020, 15 pages.
International Application Serial No. PCT/US2019/025202, International Preliminary Report on Patentability dated Oct. 15, 2020, 12 pages.
International Application Serial No. PCT/US2019/025218, Invitation to Pay Additional Fees dated Jun. 25, 2019, 8 pages.
International Application Serial No. PCT/US2019/029795, International Preliminary Report on Patentability dated Nov. 3, 2020, 8 pages.
International Application Serial No. PCT/US2019/029795, International Search Report dated Jul. 11, 2019, 4 pages.
International Application Serial No. PCT/US2019/029798, International Preliminary Report on Patentability dated Nov. 3, 2020, 14 pages.
International Application Serial No. PCT/US2019/029798, International Search Report dated Sep. 12, 2019, 7 pages.
International Application Serial No. PCT/US2019/029798, Invitation to Pay Additional Fees dated Jul. 22, 2019, 16 pages.
International Application Serial No. PCT/US2019/029798, Written Opinion dated Sep. 12, 2019, 12 pages.
International Application Serial No. PCT/US2019/029817, International Preliminary Report on Patentability dated Nov. 3, 2020, 14 pages.
International Application Serial No. PCT/US2019/029817, International Search Report dated Sep. 23, 2019, 8 pages.
International Application Serial No. PCT/US2019/029817, Invitation to Pay Additional Fees dated Aug. 1, 2019, 15 Pages.
International Application Serial No. PCT/US2019/029817, Written Opinion dated Sep. 23, 2019, 12 pages.
International Application Serial No. PCT/US2019/029827, International Preliminary Report on Patentability dated Nov. 3, 2020, 14 pages.
International Application Serial No. PCT/US2019/029827, International Search Report dated Sep. 23, 2019, 9 pages.
International Application Serial No. PCT/US2019/029827, Invitation to Pay Additional Fees dated Jul. 23, 2019, 17 Pages.
International Application Serial No. PCT/US2019/029827, Written Opinion dated Sep. 23, 2019, 12 Pages.
International Application Serial No. PCT/US2019/029956, International Preliminary Report on Patentability dated Nov. 12, 2020, 12 pages.
International Application Serial No. PCT/US2019/029973, International Preliminary Report on Patentability dated Nov. 12, 2020, 12 pages.
International Preliminary Report on Patentability for PCT application No. PCT/US2019/025211, dated Oct. 15, 2020, 13 pages.

Ishii, et al., "Uniprot database", accession No. G2J4X6, 2011, 2 pages.
Ishizuka, H, et al., "Putrescine Oxidase of Micrococcus Rubens: Primary Structure and *Escherichia coli*", Journal of General Microbiology, vol. 139, 1993, pp. 425-432.
Juengert, J. R., et al., "Absence of ppGpp Leads to Increased Mobilization of Intermediately Accumulated Poly(3-Hydroxybutyrate) in Ralstonia eutropha HI6", Applied and Environmental Microbiology, vol. 83, Issue 13, 2017, pp. e00755-17 (1-16).
Kaddor, C, et al., "Effects of homologous phosphoenolpyruvate-carbohydrate phosphotransf erase system proteins on carbohydrate uptake and poly(3-ydroxybutyrate) accumulation in Ralstonia eutropha HI6", Appl. Environ. Microbial. vol. 77, 2011, pp. 3582-3590.
Kaddor, C, et al., "Implications of various phosphoenolpyruvate-carbohydrate phosphotransf erase system mutations on glycerol utilization and poly(3-hydroxybutyrate) accumulation in Ralstonia eutropha H16", AMB Express, vol. 1, 2011, pp. 16.
Karstens, K, et al., "Phosphotransferase protein EIIANtr interacts with SpoT, a key enzyme of the stringent response, in Ralstonia eutropha HI6", Microbiology, vol. 160, 2014, pp. 711-722.
Kaster, et al., "Increased Oxygen Transfer in a Yeast Fermentation Using a Microbubble Dispersion", Applied Biochemistry andBiotechnology, vol. 24/25, 1990, pp. 469-484 (Year: 1990).
Kazakov, A E., et al., "Comparative genomics of regulation of fatty acid and branched-chain amino acid utilization in proteobacteria", Journal of Bacteriology, vol. 191, 2009, pp. 52-64.
Kim, et al., "Effect of overexpression of Actinobacillus succinogenes phosphoenolpyruvate carboxykinase on succinate production in *Escherichia coli*", Appl Environ Microbial.70(2), Feb. 2004, pp. 1238-1241.
Kisselev, L, "Polypeptide Release Factors in Prokaryotes and Eukaryotes: Same Function, Different Structure", Structure vol. 10, 2002, pp. 8-9.
Kizer, et al., "Application of functional genomics to pathway optimization for increased isoprenoid production", Appl Environ Microbial 74(10) doi: 10.1128/AEM.02750-07. Epub Mar. 14, 2008, May 2008, pp. 3229-3241.
Krausse, et al., "Essential role of the hprK gene inRalstonia eutropha HI6", J Mol Microbial Biotechnol, vol. 17, 2009. pp. 146-152.
Kyte, Jack, et al., "A Simple Method for Displaying the Hydropathic Charcter of a Protein", Journal of Molecular Biology, 157, 1982, pp. 105-132.
Lardi, M, et al., "σ-54-Dependent Response to Nitrogen Limitation and Virulence in Burkholderia cenocepacia Strain H111", Appl. Environ. Microbiol., vol. 81, Issue 12, 2015, pp. 4077-4089.
Lee, et al., "Microbial Production of Ethanol from Acetate by Engineered Ralstonia Eutropha", Biotechnology and Bioprocess Engineering, vol. 21, 2016, pp. 402-407.
Lee, et al., "Regulation of poly-β-hydroxybutyrate biosynthesis by nicotinamide nucleotide in Alcaligene eutrophus", FEMS Microbiological letters, vol. 131, 1995, pp. 35-39.
Lee, J N., et al., "Metabolic Engineering of Pentose Phosphate Pathway in Ralsonia eutropha for Enhanced Biosynthesis of poly-β-hydroxybutyrate", Biotechnology Progress, vol. 19, Issue 5, 2003, pp. 1444-1449.
Lenczak, J. L., et al., "High cell density strategy for poly(3-hydroxybutyrate) production by Cupriavidus necator", Brazilian Journal of Chemical Engineering, vol. 28, Issue 4, 2011, pp. 585-596.
Leyn, et al., "Control of proteobacterial centralcarbon metabolism by the HexR transcriptionalregulator: a case study in Shewanella oneidensis", Journal of Biological Chemistry, vol. 286, Issue 41, 2011, pp. 35782-35794.
Leyn, S A., et al., "Comparative genomics and evolution of transcriptional regulons in Proteobacteria", Microbial Genomics, 2016, pp. 1-15.
Li, Z J., et al., "Overexpression of NAD kinase in recombinant *Escherichia coli* harboring the phbCAB operon improves poly(3-hydroxybutyrate) production", Appl Microbial Biotechnol., vol. 83, Issue 5, 2009, pp. 939-947.
Lin, S, et al., "Biotin Synthesis Begins by Hijacking the Fatty Acid Synthesis Pathway", Nature Chemical Biology, vol. 6, No. 9, Sep. 2010, pp. 682-688.

(56) References Cited

OTHER PUBLICATIONS

Liu, X, "Comparative analysis of genes frequently regulated by drugs based on connectivity map transcriptome data", PLoS One, vol. 12, Issue 6, 2017, pp. e0179037 (1-13).
Lu, et al., "Studies in the production of branched-chain alcohols in engineered Ralstonia eutropha", Bioenergy and Biofuels, 96, 2012, 283-297.
Lu, et al., "Studies on the Production of Branched-chain Alcohols in Engineered Ralstonia Eutropha", Appl, Microbial, Biotechnol, vol. 96, No. 1, 2012, 15 pgs.
Lucas, et al., "Gen Bank accession No. ACU95033", Aug. 26, 2009, p. 1.
March, J C., et al., "Expression of an anaplerotic enzyme, pyruvate carboxylase, improves recombinant protein production in *Escherichia coli*", Applied and Environmental Microbiology, vol. 68, Issue 11, 2002, pp. 5620-5624.
McKinlay, J. B., et al., "Carbon dioxide fixation as a central redox cofactor recycling mechanism in bacteria", PNAS, vol. 107, Issue 26, 2010, pp. 11669-11675.
Meng, J, et al., "High-yield anaerobic succinate production by strategically regulating multiple metabolic pathways based on stoichiometric maximumin *Escherichia coli*", Microbial Cell Factories, vol. 15, 2016, 13 pgs.
Myers, Eugene, et al., "Optimal alignments in linear space", Computer Applications in the Biosciences, vol. 4, 1988, pp. 11-17.
Needleman, Saul, et al., "A general method applicable to the search for similarities in amino acid sequence of two proteins", Journal of Molecular Biology, vol. 48, Issue 3, 1970, pp. 443-453.
NETL brochure, "Syngas composition", accessed online on (https://www.netl.doe.gov/research/coal/energy-systems/gasification/gasifipedia/syngas-composition, Jul. 3, 2021, pp. 2. (Year: 2021).
Obruca, S, et al., "Application of random mutagenesis to enhance the production of polyhydroxyalkanoates by Cupriavidus necator H16 on waste frying oil", World J Microbiol Biotechnol, 2013, vol. 29, 2013, pp. 2417-2428.
Olaya-Abril, et al., "Poly(3-hydroxybutyrate) hyperproduction by a global nitrogen regulator NtrB mutant strain of Paracoccus denitrificans PD1222", FEMS Microbiology Letters, vol. 365:fnx251, 2008, 8 pgs.
Orita, L, et al., "Identification of mutation points in Cupriavidus necator NCIMB 11599 and genetic reconstitution of Glucose-utilization ability in wild strain H16 for polyhydroxyalkanoate production", Journal of Bioscience and Bioengineering, vol. 113, Issue 1, 2012, pp. 63-69.
Papagiani, M, "Recent advances in engineering the central carbon metabolism of industrially important bacteria", Microbial Cell Factories, vol. 11, 2012, 13 pgs.
Park, J S., et al., "Metabolic Characteristics of Isocitrate Dehydrogenase Leaky Mutant of Alcaligene eutrophus and its Utilization for Poly-Hydroxybutyrate Production", Journal of Fermentation and Bioengineering, 1996, vol. 81, Issue 3, 1996, pp. 197-205.
Park, S, et al., "Oxaloacetate and malate production in engineered *Escherichia coli* by expression of codon-optimized phosphoenolpyruvate carboxylase2 gene from Dunaliella salina", Bioprocess Biosyst Eng., vol. 36 Issue 1, 2013, pp. 127-131 (Abstract Only).
Pearson, William R.., et al., "Improved tools for biological sequence comparison", Proc Natl Acad Sci U S A, 85(8), 1988, pp. 2444-2448.
Persuhn, D C., et al., "The transcriptional activator NtrC controls the expression and activity of glutamine synthetase in Herbaspirillum seropedicae", FEMS Microbiology Letters, vol. 192, 2000, pp. 217-221.
Pohlmann, A, et al., "Genome sequence of the bioplastic-producing "Knallgas" bacterium Ralsonia eutropha H16", Nature Biotechnology, vol. 24, No. 10, 2007, pp. 1257-1262.
Prather KLJ et al. De nova biosynthetic pathways: Rational design of microbial chemical factories. Current Opinion in Biotechnology, 2008. 19:468-47 4 (Year: 2008).
Przybylski, et al., "Synthesis of the Building Block 2-Hydroxyisobutyrate from Fructose and Butyrate by Cupriavidus Necator H16", Appl, Microbial, Biotechnol, vol. 97, 2013, pp. 8875-8885.
Qi, et al., "Model-driven redox pathway manipulation for improved isobutanol production in Bacillus subtilis complemented with experimental validation and metabolic profiling analysis", PLoS One, vol. 9, Issue 4, e93815, 2014, pp. 1-11.
Raberg, M, "Ralstoni a eutropha H16 in progress: applications beside PHAs and establishment as production platform by advanced genetic tools", Critical Reviews in Biotechnology, vol. 38, Dec. 12, 2017, pp. 494-510 (Abstract Only).
Rosa, L T., et al., "Tripartite ATP-Independent Periplasmic (TRAP) Transporters and Tripartite Tricarboxylate Transporters (TTT): From Uptake to Pathogenicity", Frontiers in Microbiology, vol. 8,, 2018, 16 pgs.
Sacamboio, E. N. M., et al., "The transcriptional regulator NtrC controls glucose-6-phosphate dehydrogenase expression and polyhydroxybutyrate synthesis through NADPH availability in Herbaspirillum seropedicae", Scientific Reports, vol. 7, Article No. 13546, 2017, pp. 1-12.
Sadowski, M I., et al., "The sequence-structure relationship and protein function prediction", Current Opinion in Structural Biology 19, 2009, pp. 357-362.
Sanchez, A. M., et al., "Effect of overexpression of a soluble pyridine nucleotide transhydrogenase (UdhA) on the production of poly(3-hydroxybutyrate) in *Escherichia coli*", Biotechnol Prog., vol. 22, Issue 2, 2006, pp. 420-425 (Abstract Only).
Saur, U, et al., "The PEP-pyruvate-oxaloacetate node as the switch point for carbon flux distribution in bacteria", FEMS Microbiology Reviews, vol. 29, Issue 4, 2005, pp. 765-794.
Schlegel, H. G., et al., "Formation of the Dehydroganses for Lactate, Ethanol and Butanediol in the Strictly Aerobi Bacterium Alcaligene eutrophus", Microbiology, vol. 117, 1980, pp. 475-481.
Schobert, P, et al., "Unusual C3 and C4 metabolism in the chemo-autotroph Alcaligenes eutrophus", Journal of Bacterialogy, vol. 159, Issue 1, 1984, pp. 167-172.
Schramke, et al., "Revisiting Regulation of Potassium Homeostasis in *Escherichia coli*: The Connection to Phosphate Limitation", Wiley Microbiologyopen, vol. 6, No. 3, 2017, pp. 1-16.
Schwartz, E, et al., "A proteomic view of the facultatively chemolithoautotrophic lifestyle of Ralstonia eutropha H16", Proteomics, vol. 9, Issue 22, 2009, pp. 5132-5142 (Abstract Only).
Seffernick, J L., et al., "Melamine Deaminase and Atrazine Chlorohydrolase: 98 Percent Identical but Functionally Different", Journal of Bacteriology, 183, 2001, pp. 2405-2410.
Segura, D, et al., "Inactivation of pycA, encoding pyruvate carboxylase activity, increases polybeta-hydroxybutyrate accumulation in Azotobacter vinelandii on solid medium", Appl Microbial Biotechnol, pp. 65, Issue 4, 2004, pp. 414-418.
Sekar, B S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate", dehydrogenase ( gnd), Biotechnology for Biofuels, vol. 10, 85, 2017, 12 pgs.
Shang, et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-14197.
Shulman, Andrew, et al., "Structural Determinants of Allosteric Ligand Activation in RXR Heterodimers", Cell, vol. 116, 2004, pp. 417-429.
Singh, et al., "Protein Engineering Approaches in the Post-Genomic Era", Curr Protein Pept Sci., 2017, pp. 1-11.
Slabu, et al., "Discovery, Engineering and Synthetic Application of Transaminase Biocatalysts", ACS Catalysis 7, 2017, pp. 8263-8284.
Smith, Temple, et al., "Comparison of biosequences", Advances in Applied Mathematics, 2(4), Dec. 1981, pp. 482-489.
Steinbuchel, A, et al., "A multifunctional fermentative alcohol dehydrogenase from the strict aerobe Alcaligenes eutrophus: purification and properties", Eur J Biochem, vol. 141, Issue 3, 1984, pp. 555-564.

(56) References Cited

OTHER PUBLICATIONS

Stokke, R, et al., "Biochemical characterization of isocitrate dehydrogenase from Methylococcus capsulatus reveals a unique NAD+-dependent homotetrameric enzyme", Arch Microbial., vol. 187, Issue 5, 2007, pp. 361-370.

Sun, J, et al., "Involvement of glnB, glnZ, and glnD genes in the regulation of poly-3-hydroxybutyrate biosynthesis by ammonia in Azospirillum brasilense Sp7", Appl. Environ. Microbial, vol. 68, Issue 2, 2002, pp. 985-988.

Sun, J, et al., "The ntrB and ntrC genes are involved in the regulation of poly-3-hydroxybutyrate biosynthesis by ammonia in Azospirillum brasilense Sp7", Appl. Environ. Microbial., vol. 66, Issue 1, 2000, pp. 113-117.

Tan, Z, et al., "Activating phosphoenolpyruvate carboxylase and phosphoenolpyruvate carboxykinase in combination for improvement of succinate production", Appl. Environ. Microbial., vol. 79, Issue 16, 2013, pp. 4838-4844.

Tang, et al., "Identification of Dehalobacter reductive Dehalogenases that catalyse dechlorination of chlorofom, 1,1,1-tricloroethane and 1,1-dicloroethane", Phil Trans R Soc B 368:20120318, 2013, pp. 1-10.

Uniprot database, entry A0A0U2WHG0, Mar. 2016, 4 pages.

Valderrama, J A., et al., "AccR is a master regulator involved in carbon catabolite repression of the anaerobic catabolism of aromatic compounds in *Azoarcus* sp. CIB", Journal of Biological Chemistry, vol. 289, Issue 4, 2014, pp. 1892-1904.

Vemuri, G N., "Physiological response of central metabolism in *Escherichia coli* to deletion of pyruvate oxidase and introduction of heterologous pyruvate carboxylase", Biotechnology and Bioengineering, vol. 90, Issue 1, 2005, pp. 64-76.

Vollbrecht, D, et al., "Excretion of Metabolites by hydrogen Bacteria III. D(-)-3-hydroxybutanoate", European J. Appl. Microbiol. Biotechnol, vol. 7, 1979, pp. 259-266.

Vollbrecht, et al., "Excretion of Metabolites by Hydrogen Bacteria I. Autotrophic and Heterotrophic Fermentations", European journal of applied microbiology and biotechnology, vol. 6, Issue 2, 1978, pp. 145-155.

Vollbrecht, et al., "Excretion of Metabolites by Hydrogen Bacteria II. Influences of Aeration, pH, Temperature, and Age of Cells", European Journal of Applied Microbiology and Biotechnology, vol. 6, Issue 2, 1978, pp. 157-166.

Vollbrecht, et al., "Excretion of Metabolites by Hydrogen Bacteria IV. Respiration Rate-dependent Formation of Primary Metabolites and of Poly-3-Hydroxybutanoate", European Journal of Applied Microbiology and Biotechnology, vol. 7, Issue 3, 1979, pp. 267-276.

Volodina, E, et al., "Characterization of propionate GoA-transferase from Ralstonia eutropha HI6", Appl Microbial, Biotechnol, vol. 98, Issue 8, 2014, pp. 3579-3589.

Wang, et al., "Poly(3-Hydroxybutyrate) Production with High Productivity and High Polymer Content by a Fed-Batch 23 Culture of Alcaligenes latus under Nitrogen Limitation", Applied and Environmental Microbiology, vol. 63, No. 9, Sep. 1997, pp. 3703-3706.

Wang, R, et al., "Isocitrate dehydrogenase from *Streptococcus mutans*: biochemical properties and evaluation of a putative phosphorylation site at Ser102", PLoS One, vol. 8, Issue 3, 2013, pp. e58918 (1-8).

Weinberg, Z, et al., "Identification of 22 candidate structured RNAs in bacteria using the Cmfinder comparative genomics pipeline", Nucleic Acids Research, vol. 35,, 2007, pp. 4809-4819.

Welden, et al., "Cation Transport in *Escherichia coli* Vii. Potassium Requirement for Phosphate Uptake", The Journal of General Physiology, vol. 50, No. 6, 1967, pp. 1641-1661.

Whisstock et al., "Prediction of protein function from protein sequence and structure", Quarterly Reviews of BioPhysics, vol. 36, Issue 3, pp. 307-340 (2003).

Winnen, B, et al., "The tripartite tricarboxylate transporter (TIT) family", Res. Microbial, vol. 154, Issue 7, 2003, pp. 457-465.

Witkowski, A, et al., "Conversion of a β-Ketoacyl Synthase to a Malonyl Decarboxylase by Replacement of the Active-Site Cysteine with Glutamine", Biochemistry, 38, 1999, pp. 11643-11650.

Wu, M-C, et al., "A Novel Type II NAD+-Specific Isocitrate Dehydrogenase from the Marine Bacterium Congregibacte toralis KT71", PLoS One., vol. 10, Issue 5, 2015, pp. 1-17.

Youngquist, et al., "Functional Genomics Analysis of Free Fatty Acid Production under Continuous Phosphate Limiting Conditions", J. Ind. Microbial. Biotechnol., vol. 44, May 2017, pp. 759-772.

Zhang M et al. Propagated Perturbations from a Peripheral Mutation Show Interactions Supporting WW Domain Thermostablity, 2018, Structure. 26, 1474-1485. (Year: 2018).

Huang et al., "Bacterial and Yeast Cultures—Process Characteristics, Products, and Applications", Bioprocessing for Value-Added Products from Renewable Resources, pp. 185-223, Dec. 2007 (Year: 2007).

Non-Final Rejection received for U.S. Appl. No. 16/372,092, dated Nov. 26, 2021, 10 Pages.

Ghosalkar et al., "Oxygen Uptake Rate Measurement by Modified Dynamic Method and Effect of Mass-Transfer Rates on Growth of Pichia Stipitis : Modeling and Experimental Data Comparison", Austin Journal of Biotechnology & Bioengineering, vol. 3, Issue 3, 2016, 6 pages.

Kirk et al., "Quantification of the oxygen uptake rate in a dissolved oxygen-controlled oscillating jet-driven microbioreactor", Journal of Chemical Technology & Biotechnology, vol. 91, 2016, pp. 823-831.

Non-Final Office Action received for U.S. Appl. No. 16/372,092, dated Sep. 15, 2022, 11 pages.

Non-Final office action for U.S. Appl. No. 16/399,145 dated Jul. 27, 2023, 29 pages.

PTO STIC search in GenEmbl run on Jun. 27, 2022, pp. 1-6.

Yuzawa Satoshi et al., "Synthetic biology of polyketide synthases", Journal of industrial microbiology & biotechnology, vol. 45, No. 7, Feb. 9, 2018, pp. 621-633.

Advisory Action received for U.S. Appl. No. 16/372,092, mailed on Oct. 7, 2021, 3 pages.

Advisory Action received for U.S. Appl. No. 16/372,099, mailed on Feb. 22, 2022, 3 pages.

Advisory Action received for U.S. Appl. No. 16/399, 145, mailed on Mar. 4, 2022, 4 pages.

U.S. Appl. No. 16/372,083, Notice of Allowability mailed Sep. 22, 2021, 5 pages.

U.S. Appl. No. 16/372,083, Notice of Allowance mailed Aug. 31, 2021, 9 pages.

U.S. Appl. No. 16/372,083, Response filed Jul. 27, 2021 to Non-Final Office Action mailed Apr. 27, 2021, 11 pages.

U.S. Appl. No. 16/372,083, Supplemental Amendment filed for Non-Final Office Action mailed Apr. 27, 2021, 8 pages.

U.S. Appl. No. 16/372,092, Response filed Sep. 21, 2021 to Final Office Action mailed Jul. 26, 2021, 11 pages.

Aspartate aminotransferase family protein [Rhodobacteraceae bacterium CH30], GenBank: RQW28969.1, Dec. 2, 2018, 2 pages.

Baltz et al. "Manual of Industrial Microbiology and Biotechnology", ASM Press, 2010, 4 Pages (Abstract).

Berg et al."Biochemistry 5th ed.", W H Freeman and Company, 2002, 1 Page (Abstract).

Cavalheiro JMBT et al. Poly(3-hydroxybutyrate) production by Cupriavidus necator using waste glycerol, Process Biochemistry, vol. 44, 2009, pp. 509-515.

Database UniProt, "RecName: Full=Thiopurine S-methyltransferase [ECO:0000256|HAMAPRule:MF_00812, ECO:0000256|SAAS:SAAS00896910}; EC=2.1.1.67; AltName: Full=Thiopurine methyltransferase", EBI accession No. Uniprot:A0A1L8MA47 Database accession No. A0A1L8MA47, Mar. 15, 2017, 04 Pages.

Database UniProt, "SubName: Full=Acyl-ACP thioesterase ", retrieved from EBI accession No. EBI accession No. Uniprot:R7CHF5 Database accession No. R7CHF5, Jul. 24, 2013, 03 Pages.

Database UniProt,"RecName: Full=Thiopurine S-methyltransferase [ECO:0000256|HAMAPRule:MF_00812, ECO:0000256|SAAS:SAAS00896910}; EC=2.1.1.67; AltName: Full=Thiopurine methyltransferase ",EBI accession No. Uniprot:A0A009ZVV4 Database accession No. A0A009ZVV4, Jun. 11, 2014, 04 Pages.

(56) References Cited

OTHER PUBLICATIONS

Final office action received for U.S. Appl. No. 16/372,092, mailed on Dec. 7, 2023, 14 pages.
Final office action received for U.S. Appl. No. 16/398,351, mailed on Feb. 28, 2022, 11 pages.
Final office action received for U.S. Appl. No. 16/398,351, mailed on Jul. 2, 2021, 24 pages.
Final office action received for U.S. Appl. No. 16/398,401, mailed on Feb. 6, 2023, 25 pages.
Final Rejection received for U.S. Appl. No. 16/372,099, mailed on Dec. 21, 2021, 17 pages.
Final Rejection received for U.S. Appl. No. 16/399,145, mailed on Dec. 22, 2021, 20 pages.
Folsom, J.P. et al., "Physiological and Proteomic Analysis of Escherichia coli Iron-Limited Chemostat Growth," Journal of Bacteriology, vol. 196, No. 15, Aug. 2014, pp. 2748-2761.
GenBank A6VKV4 , GenBank, 2012, pp. 1-3.
GenBank Q0K4C1, GenBank, 2006, 1 page.
GenBank Q0K790, GenBank, 2006; 1 page.
GenBank Q0K7M4, GenBank, 2006, 1 page.
GenBank Q0KC80, GenBank, 2006, pp. 1-2.
GenBank Q2Z1A9, GenBank, 2006, 1 page.
GenBank Q46WX6, GenBank, 2006; pp. 1-2.
GenBank Q474V2, GenBank, 2006; pp. 1-2.
GenBank Q0K5F4, GenBank, 2006, 1 page.
Harder et al., "Physiological responses to nutrient limitation", Annual Review of Microbiology, vol. 37, 1983, pp. 1-23.
International Search Report and Written Opinion for International Application Serial No. PCT/US2019/025189, mailed on Jul. 2, 2019, 12 pages.
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Kihlberg,"The Microbe as a Source of Food" Annual Review of Microbiology, vol. 26, 1972, pp. 427-466.
Inui, M., et al., Metabolic Engineering of Corynebacterium glutamicum for Fuel Ethanol Production under Oxygen Deprivation Conditions.. J. Mol. Microbiol. Biotechnol., vol. 8, 2004, pp. 243-254.
Non-Final Action received for U.S. Appl. No. 16/398,351, mailed on Jul. 5, 2022, 12 Pages.
Non-Final Action received for U.S. Appl. No. 16/398,401, mailed on Sep. 1, 2022, 32 pages.
Non-Final Rejection received for U.S. Appl. No. 16/372,092, mailed on Sep. 15, 2022, 11 Pages.
Non-Final office action received for U.S. Appl. No. 16/398,401 , mailed on Nov. 9, 2021, 38 pages.
Notice of Allowance received for U.S. Appl. No. 16/372,099, mailed on Apr. 15, 2022, 11 pages.
Ogawa et al.,"Role of Phosphoenolpyruvate in the NADP-Isocitrate Dehydrogenase and Isocitrate Lyase Reaction in Escherichiacoli", Journal of Bacteriology, vol. 189, No. 3, Feb. 2007, pp. 1176-1178.
Response to Final Office Action for U.S. Appl. No. 16/372,099, filed on Feb. 8, 2022, 9 pages.
Response to Final Office Action received for U.S. Appl. No. 16/399,145, filed on Feb. 22, 2022, 10 pages.
Response to Non-Final Office Action for U.S. Appl. No. 16/372,099, filed on Oct. 7, 2021, 8 pages.
Response to Non-Final Rejection for U.S. Appl. No. 16/372,092, filed on Feb. 28, 2022, 9 pages.
Stanbury et al. "Principles of Fermentation Technology", 3rd Edition, Aug. 31, 2016, 4 Pages.(Abstract).
GenBank CAQ69169.1, 2015, pp. 1-2.
GenBank Q8XWW2.1, 2015, pp. 1-2.
Non-Final Rejection received for U.S. Appl. No. 16/398,401, mailed on Jun. 22, 2023, 18 pages.
Final office action received for U.S. Appl. No. 16/372,092, mailed on Mar. 28, 2024, 12 pages.
Lopes et al., "Over-Pressurized Bioreactors: Application to Microbial Cell Cultures", American Institute of Chemical Engineers, vol. 30, No. 4, 2014, pp. 767-774.

\* cited by examiner

HIGH HYDROGEN UTILIZATION AND GAS RECYCLE

CROSS REFERENCE TO RELATED APPLICATION

The present application claims the benefit of U.S. Provisional Patent Application No. 62/650,590 filed Mar. 30, 2018, and U.S. Provisional Patent Application No. 62/650,575 filed Mar. 30, 2018, both of which are incorporated herein by reference for all purposes.

FIELD

The present disclosure relates generally to systems and methods useful for synthetic processes. In particular, the present disclosure relates to systems and methods that include a supplemented gas recycle to support bioprocesses that utilize a high amount of hydrogen.

BACKGROUND

In gas fed fermentation, volatile gases such as carbon dioxide, carbon monoxide, hydrogen, and methane are converted by microorganisms into a wide range of products such as fuel, protein, and chemical compounds, e.g., alcohols and organic acids. These products can be used by industries in the chemical, petrochemical, pharmaceutical, animal feed, environmental, and agricultural sectors. Fermentation systems involving various configurations of bioreactors are used for the generation of a diverse array of materials that include antibiotics, vaccines, synthetic biopolymers, synthetic amino acids, and edible proteins. Advantageously, gas fermentation processes can utilize a variety of feedstocks including domestic, industrial, or agricultural waste, thereby reducing reliance on fossil sources of carbon and reducing emission of greenhouse gases. Furthermore, fermentation reactions generally operate at lower reaction temperatures and pressures when compared to high temperature and pressure chemical catalytic reactions.

An example of a gas fed fermentation can be found in U.S. Patent Application Publication No. US 2012/0003706, which describes an anerobic process for converting a gas input stream comprising carbon monoxide, carbon dioxide, and hydrogen by contact with fermentation liquid into a liquid product, wherein the process controls the concentration of carbon monoxide and carbon dioxide in the fermentation vessel. The process charges the feed gas stream and a recycle gas stream to the fermentation vessel and an off-gas stream collects above the fermentation liquid. The off-gas stream flows to a gas injector that uses a recycle liquid as the motive fluid to mix the off-gas with the recycle liquid into a gas-liquid dispersion. Contact of the recycle liquid with the off-gas absorbs carbon dioxide to provide the recycle stream. A gas separation vessel separates the remainder of the off-gas into the recycle gas. Mixing the recycle gas with the gas input stream dilutes the concentration of carbon monoxide to lower the carbon monoxide concentration in the fermentation vessel. Separated recycle liquid flows to a carbon dioxide stripper for removal of carbon dioxide.

U.S. Patent Application Publication No. US 2013/0065285 includes a system for employing chemoautotrophic aerobic microorganisms to capture carbon from industrial waste. The system comprises an industrial source, such as a cement plant, and a bioreactor including the microorganisms. The bioreactor is fed the waste stream from the source, which provides carbon to the microorganisms, and is also fed hydrogen, from which the microorganisms derive their energy. Additional or alternative carbon can be provided from a gasifier fed an organic feedstock. The carbon provided to the microorganisms is converted into chemical products which can be recovered from the bioreactor. Hydrogen can be produced by electrolysis using electricity generated by a renewable energy source.

Further bioprocesses using gas fed bioreactors are described in International Patent Application Publication No. WO 2017/165244, which is directed to the conversion of gaseous carbon sources, such as syngas, producer gas, and renewable hydrogen combined with carbon dioxide, into nutritional and other useful bioproducts; and International Patent Application No. WO 2013/186340, which is directed to methods for producing 2-hydroxyisobutyric acid by contacting bacterium in an aqueous medium with a gas mixture comprising hydrogen and carbon dioxide.

Microorganisms can be grown under various engineering and physical conditions inside the gas fermenter such as agitation, mixing, aeration, pressure, shear, temperature and pH. Some microorganisms grow under anaerobic conditions while others grow under aerobic conditions. For aerobic reactions, air is generally used as the source of oxygen, but oxygen-enriched air or pure oxygen can also be used. It is generally preferable to operate at the highest possible oxygen concentration to maximize oxygen mass transfer and thereby optimize productivity. This is because the rate of oxygen mass transfer from the gas phase to the liquid phase is a known rate-limiting step for most aerobic microbial biosynthetic reactions.

Certain organisms, such as *Cupriavidus necator*, cease to function or function at very low rates below a minimum dissolved oxygen (DO) concentration because they are no longer able to metabolize oxygen at a minimal rate necessary to grow and/or generate product, and also display growth inhibition and reduced oxygen uptake rate (OUR) when DO is above a certain concentration. Accordingly, control of DO concentration within a particular range can be important to enable growth of the organism. DO concentration can also be balanced with, and in equilibrium with, the oxygen concentration in the gaseous headspace of the fermenter in which the aerobic biosynthesis occurs. The oxygen concentration in the gaseous headspace can correspond to the Limiting Oxygen Concentration (LOC) for flammability, which can be the upper control limit for the fermenter. The minimum DO concentration can be the lower control limit for the fermenter. The DO and gaseous oxygen concentration in the headspace can be difficult to control, especially as pressure is increased above atmospheric pressure and as oxygen solubility increases. Additionally, for any potentially flammable gas mixture outside of the fermenter, e.g., the fermenter broth (i.e., liquid phase), such as the fermenter headspace gas mixture, it is desirable to operate with the gaseous oxygen concentration safely below the LOC for flammability in the gaseous composition.

Therefore, the need exists for improved bioprocesses that increase the gas utilization and safety of biosynthesis reactions carried out in gas fed bioreactors.

SUMMARY

In one embodiment, the present disclosure relates to a method for improved gas utilization and off-gas recycling in a biosynthetic system. The method comprises providing a culture of an aerobic organism capable of synthesis of one or more biosynthetic products. In some embodiments, the concentration of the culture is from 10 g/L to 100 g/L. In some aspects, the culture is within a bioreactor. Optionally, the bioreactor is not actively stirred. The fermenter can be selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters. The fermenter can be a non-stirred fermenter. The fermenter can be not mechanically agitated. In some embodiments, the bioreactor has a gauge pressure ranging from 1 bar to 10 bar. The fermenter can be operated at a pressure above atmospheric pressure. The method can further comprise measuring gaseous oxygen concentration in headspace of the fermenter, and controlling the gaseous oxygen concentration to be less than 75% of the limiting oxygen concentration (LOC) of the gaseous mixture in the headspace of the fermenter. The fermenter can comprise at least two oxygen addition inlets. At least one gaseous feed stream supplied to the fermenter can be an air feed stream, an oxygen-enriched air stream, or a pure oxygen stream. The dissolved oxygen concentration can be controlled to be at a value below the transitional DO concentration, wherein the transitional DO concentration is the DO concentration at which the maximum specific OUR of the fermentation occurs. In some aspects, the bioreactor is a loop reactor. In some aspects, the bioreactor is a chemostat.

In some aspects, the organism is a genetically modified organism. Optionally, the organism is a chemoautotroph. The microorganism can be dependent on chemoautotrophic metabolism/RUBISCO. The microorganism can be a RUBISCO-containing microorganism. The microorganism can be selected from non-pathogenic members of the genera *Ralstonia, Wausteria, Cupriavidus, Alcaligenes, Burkholderia* or *Pandoraea*. In some aspects, the organism is *Cupriavidus necator* or *Cupriavidus metallidurans*. In some embodiments, the method further comprises collecting at least a portion of the one or more biosynthetic products. In some aspects, the one or more biosynthetic products comprise intracellular products such as poly(3-hydroxybutyrate). In some aspects, the one or more biosynthetic products comprise single-cell protein. In some aspects, the one or more biosynthetic products comprise extracellular products secreted from the organism into the culture.

The method further comprises introducing a supply gas to the culture, wherein the supply gas can comprise a feed gas and a recycle gas. In some embodiments, the supply gas further comprises an oxygen make-up gas. Optionally, the concentration of oxygen in the oxygen make-up gas is greater than 50% (v/v). In some embodiments, the supply gas further comprises a carbon dioxide make-up gas. In some embodiments, the supply gas further comprises a hydrogen make-up gas. Optionally, the concentration of hydrogen in the hydrogen make-up gas is greater than 50% (v/v). In some embodiments, the oxygen make-up gas is introduced into the bioreactor at a location separate from a location at which the hydrogen make-up gas is introduced into the bioreactor. In some embodiments, the concentration of oxygen in the supply gas is greater than the limiting oxygen concentration for the supply gas composition. The concentration of nitrogen in the supply gas can be less than 5% (v/v), e.g., less than 1% (v/v) or less than 0.1% (v/v). In some aspects, the supply gas comprises oxygen. Optionally, the concentration of oxygen in the supply gas ranges from 2% (v/v) to 20% (v/v). In some aspects, the supply gas comprises hydrogen. Optionally, the concentration of hydrogen in the feed gas ranges from 10% (v/v) to 95% (v/v). In some aspects, the supply gas comprises carbon dioxide. Optionally, the concentration of carbon dioxide in the supply gas ranges from 1% (v/v) to 45% (v/v), e.g., from 1% (v/v) to 15% (v/v). In some embodiments, the synthesis has a stoichiometric hydrogen requirement and a stoichiometric oxygen requirement, and the ratio of (1a) the concentration of hydrogen in the supply gas to (1b) the concentration of oxygen in the supply gas is greater than the product of (2) the ratio of (2a) the stoichiometric hydrogen requirement to (2b) the stoichiometric oxygen requirement and (3) the ratio of (3a) the Henry's law solubility constant of hydrogen in the culture to (3b) the Henry's law solubility constant of oxygen in the culture. In some embodiments, the synthesis has a stoichiometric carbon dioxide requirement and a stoichiometric oxygen requirement, and the ratio of (1a) the concentration of carbon dioxide in the supply gas to (1b) the concentration of oxygen in the supply gas is greater than the product of (2) the ratio of (2a) the stoichiometric carbon dioxide requirement to (2b) the stoichiometric oxygen requirement and (3) the ratio of (3a) the Henry's law solubility constant of carbon dioxide in the culture to (3b) the Henry's law solubility constant of oxygen in the culture. The concentration of a target component in the recycle gas can be within a target range, wherein the target component can be hydrogen, carbon dioxide, or oxygen. In some aspects, the feed gas has a flow rate from 0.5 standard liter/minute/(liter of culture) to 5 standard liter/minute/(liter of culture).

The method further comprises producing, with the culture, an off-gas comprising, for example, unreacted hydrogen, carbon dioxide, and/or oxygen. In some aspects, the molar flow rate of hydrogen in the off-gas is less than 40% of the molar flow rate of hydrogen in the supply gas. In some embodiments, the concentration of oxygen in the off-gas is less than the limiting oxygen concentration for the off-gas composition. Optionally, the producing comprises biosynthesis of at least one of the one or more biosynthetic products. The method further comprises measuring the concentration of the target component in the off-gas. Optionally, the method further comprises measuring the flow rate of the off-gas. The method further comprises calculating an amount of a supplemental gas to be added to a portion of the off-gas to form the recycle gas having the target concentration range of the target component. In some aspects, the supplemental gas has a composition substantially identical to the composition of the feed gas. In some aspects, the portion of the off-gas combined with the supplemental gas is less than 99% (v/v) of the off-gas, and off-gas not combined with the supplemental gas is a purge gas. The method further comprises combining the calculated amount of the supplemental gas and the portion of the off-gas to form the recycle gas.

BRIEF DESCRIPTION OF THE FIGURES

The present application includes the following figures. The figures are intended to illustrate certain embodiments and/or features of the methods, and to supplement any description of the methods. The figures do not limit the scope of the methods, unless the written description expressly indicates that such is the case.

DETAILED DESCRIPTION

Figure 1:
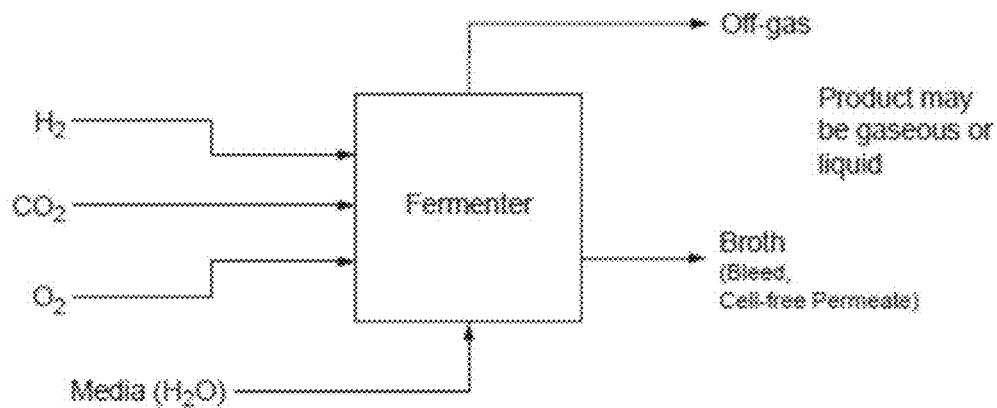
FIG. 1 is a block diagram showing a comparative gas fermentation stream arrangement without off-gas recycle.
Figure 2:
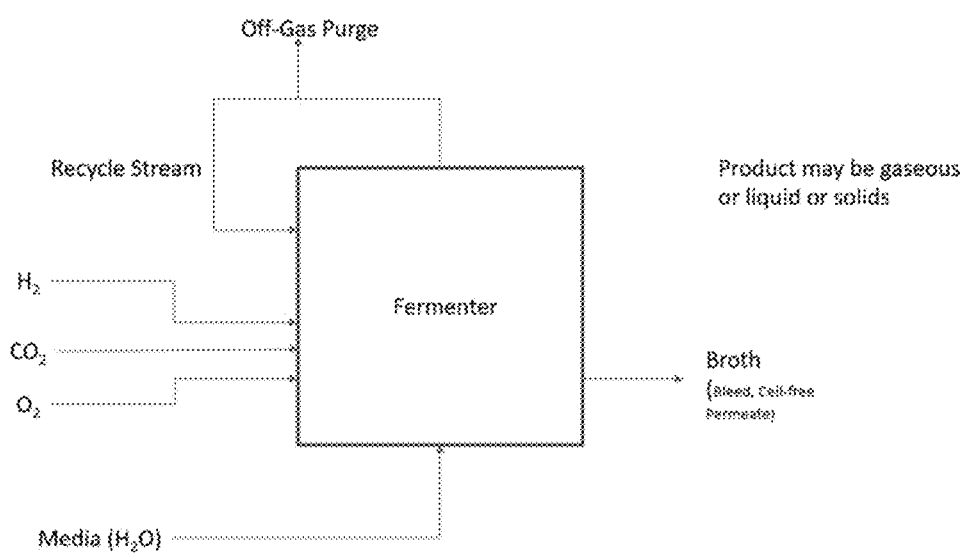
FIG. 2 is a block diagram showing a gas fermentation stream arrangement with off-gas recycle and purge in accordance with a provided embodiment.

The present disclosure generally relates to systems and methods that, when employed in synthetic processes, provide advantageous improvements in the conversion of hydrogen to one or more products. For example, for an aerobic biosynthetic process including organisms capable of converting a carbon source and hydrogen to a desired bioproduct, the efficient and adequate supply of these gas substrates, as well as oxygen, to the organism can be critical in determining the gas conversion efficiency and productivity of the bioproduct synthesis. Any increases realized in efficiency or productivity can deliver process benefits associated with greater product amounts, reduced gas feedstock requirements, decreases in bioreactor operation time, or other advantages directly related to the commercial viability of the process, especially at industrial scale.

Conventionally, gas fed bioreactors supply hydrogen, carbon, and oxygen to cultures in ratios and amounts that must simultaneously meet several competing demands. The feed gas components must be provided to the culture in concentrations required by those metabolic reactions of the organism necessary for cell maintenance. As the culture organisms serve as catalysts for the desired product synthesis, a stable and active culture is needed to provide for product generation. However, it has been demonstrated that process operating regimes characterized by high concentrations of some feed gas components can lead to the poisoning of the cell culture, whereas operating conditions having low feed gas component concentrations can be associated with cultures prone to genetic instability or an increased likelihood of contamination by competing strains or microorganism types. Additionally, the feed gas components must meet the stoichiometric demands of the desired product biosynthesis. If one or more biosynthesis substrates becomes limiting, then the reaction rates can decrease, and other substrates can pass through the bioreactor unconverted. These scenarios lead to undesired decreases in process efficiencies and productivities. Moreover, feed gas compositions must also be designed with consideration of safety issues associated with the blends of constituent components. For example, a gas containing amounts and ratios of hydrogen and oxygen above certain thresholds can pose a significantly greater risk of combustion or explosion.

Furthermore, for cost reasons, it is typical for the oxygen required by aerobic fermentations to be supplied by introducing compressed air as an oxygen source. It is common for such air fed biosynthesis reactions to, for example, utilize a single pass and have hydrogen conversion rates that are below 60%. It is known that multiple passes can be carried out in the gas fermenter by recycling some of the unreacted or product gas phase components, however conventional approaches to the recycling of gas in chemoautotrophic fermentations involve air feeds that require high pressure and/or expensive gas separation steps to remove, for example, unreacted nitrogen that builds up within a recycle stream. These gas compression and separation steps can be prohibitively expensive, severely limiting the economic viability of the overall biosynthetic process.

The inventors have now discovered that through the use of particular methods that employ multiple feed gas streams, advantageous improvements in hydrogen conversion rates, and process safety and costs can be surprisingly realized. Importantly, these improvements are achieved in processes that do not require high pressures or additional gas separation steps that can cause the economics of a process to suffer. In particular, it has been found that by using an oxygen or highly oxygen-rich supply gas or make-up gas with greatly reduced nitrogen concentrations, and by collecting at least a portion of the off-gas of a biosynthesis reaction, measuring the concentration of a target component within the off-gas portion, and combining the off-gas portion with a determined quantity of a supplement gas, a recycle gas can be formed that has a concentration of the target component within a target range. In this way, the target component, e.g., hydrogen, oxygen, or carbon dioxide, can be supplied to the biosynthesis reaction in an improved fashion that can lead to efficiency and productivity gains. In some embodiments, the use of these methods advantageously allows for more than 60% of the hydrogen fed to the culture to be converted overall. In certain aspects, the use of these methods can also increase the yield of one or more biosynthesis products relative to the yield that can be attained in an otherwise similar system not using these methods.

The economic advantages are particularly unexpected in that they are achieved using a process that involves costly gas feeds having high concentrations of hydrogen and higher purity oxygen, rather than a relatively less expensive air or nitrogen gas feed with reduced hydrogen gas feed concentration. Because of the additional expense associated with the gas feeds of the methods and systems disclosed herein, the raw material cost associated with a single reaction pass can be higher than for a comparative air fed gas reaction. However, the inventors have surprisingly found that because the costlier gas feeds include lower concentrations of unreacted components, such as nitrogen, the need for expensive gas separation processes to remove build-up of these components and permit recycling is reduced or eliminated. Relatedly, the percentage of the off-gas of the fermentation that can be recycled can be increased to levels approaching or as high as 100%. This larger degree of gas substrate recycling, combined with the higher concentrations of gaseous substrates that can be included in the gas supply, can increase hydrogen utilization and boost overall productivity, such that the provided multi-pass recycle systems can be significantly more economical and efficient than other previously known gas fermentations.

Another advantage provided by the disclosed methods is that the use of a supply gas comprising multiple streams allows for the addition to the culture of an oxygen amount above the limiting oxygen concentration (LOC) for the overall supply gas composition, used herein to refer to the concentration of oxygen below which combustion is not possible. This can provide greater flexibility in the operation of the bioprocess, without compromising process safety.

In one embodiment, a method for gas utilization and recycling in a biosynthetic system, e.g., a gas fermentation biosynthetic system, is disclosed. The method includes providing a culture of an organism capable of synthesis of one or more biosynthetic products. A supply gas is introduced to the culture to provide substrates necessary for the maintenance of the culture and the generation of the biosynthetic products, wherein the supply gas includes a recycle gas. The supply gas, i.e., the combination of all gases fed to the culture, can be introduced into a bioreactor containing the culture. In certain aspects the supply gas is introduced into the liquid culture by a suitable device in order to create microbubbles and enhance the gas-liquid interface between gas phase and bulk liquid. In certain aspects, the methods include a continuous fermentation, such as in a loop reactor or a chemostat, in which gases and liquid nutrients are continuously fed to the bioreactor as off-gases and at least a portion of the culture is continuously removed from the bioreactor. In some embodiments, a portion of the biomass in the removed culture is returned to the bioreactor.

The supply gas of the method can be selected to have a composition beneficial for the biosynthetic system. For example, the composition of the supply gas can be selected to improve the growth rate of the organisms in the culture or the generation of desired products. The composition of the supply gas can be selected to improve the maintenance and stability of the organisms in the culture. In certain aspects, the composition of the supply gas can be selected to improve the rate of product formation by the organisms in the culture. In some embodiments, the supply gas can be substantially free of one or more selected components. For example, the supply gas can be substantially free of nitrogen. In other words, the concentration (v/v) of nitrogen in the supply gas can be less than 10%, e.g., less than 8%, less than 6%, less than 5%, less than 4%, less than 3%, less than 2%, less than 1%, less than 0.8%, less than 0.6%, less than 0.5%, less than 0.4%, less than 0.3%, less than 0.2%, or less than 0.1%.

In certain aspects, the supply gas composition can be selected to include one or more nutrients of the culture organism, or one or more substrates or cofactors of metabolic or biosynthetic reactions of the organism. The supply gas includes one or more target components, each independently having a concentration in the supply gas within a selected target concentration range, and each independently having a flow rate in the supply gas within a selected target flow rate range. The target component of the supply gas can be any component selected to be added to the biosynthetic system. The target component can be, for example, one of the nutrients and substrates provided to the culture in the supply gas. For example, the target component can be a nutrient required for growth of the organism of the culture. The target component can be a substrate or cofactor of one or more metabolic reactions of the organism leading to synthesis of the one or more biosynthetic products. In some embodiments, the target component is hydrogen, oxygen, or carbon dioxide. In some embodiments, the target components include each of hydrogen, oxygen, and carbon dioxide.

In some embodiments, the supply gas includes oxygen. The concentration (v/v), e.g., target concentration, of oxygen in the supply gas can be, for example, from 2% to 20%, e.g., from 2% to 12.8%, from 3.8% to 14.6%, from 5.6% to 16.4%, from 7.4% to 18.2%, or from 9.2% to 20%. In terms of upper limits, the supply gas oxygen concentration can be less than 20%, e.g., less than 18.2%, less than 16.4%, less than 14.6%, less than 12.8%, less than 11%, less than 9.2%, less than 7.4%, less than 5.6%, or less than 3.8%. In terms of lower limits, the supply gas oxygen concentration can be greater than 2%, e.g., greater than 3.8%, greater than 5.6%, greater than 7.4%, greater than 9.2%, greater than 11%, greater than 12.8%, greater than 14.6%, greater than 16.4%, or greater than 18.2%. Higher concentrations, e.g., greater than 20%, and lower concentrations, e.g., less than 2%, are also contemplated.

In some embodiments, the supply gas includes carbon dioxide. The concentration (v/v), e.g., target concentration, of carbon dioxide in the supply gas can be, for example, from 1% to 50%, e.g., from 1% to 30%, from 5% to 35%, from 10% to 40%, from 15% to 45%, or from 20% to 50%. The concentration of carbon dioxide in the supply gas can be from 1% to 15%, e.g., from 1% to 9.4%, from 2.4% to 10.8%, from 3.8% to 12.2%, from 5.2% to 13.6%, or from 6.6% to 15%. In terms of upper limits, the supply gas carbon dioxide concentration can be less than 50%, e.g., less than 45%, less than 40%, less than 35%, less than 30%, less than 25%, less than 20%, less than 15%, less than 13.6%, less than 12.2%, less than 10.8%, less than 9.4%, less than 8%, less than 6.6%, less than 5.2%, less than 3.8%, or less than 2.4%. In terms of lower limits, the supply gas carbon dioxide concentration can be greater than 1%, e.g., greater than 2.4%, greater than 3.8%, greater than 5.2%, greater than 6.6%, greater than 8%, greater than 9.4%, greater than 10.8%, greater than 12.2%, greater than 13.6%, greater than 15%, greater than 20%, greater than 25%, greater than 30%, greater than 35%, greater than 40%, or greater than 45%. Higher concentrations, e.g., greater than 50%, and lower concentrations, e.g., less than 1%, are also contemplated.

In some embodiments, the supply gas includes hydrogen. The concentration (v/v) of hydrogen in the supply gas can be, for example, from 10% to 95%, e.g., from 10% to 61%, from 18.5% to 69.5%, from 27% to 78%, from 35.5% to 86.5%, or from 44% to 95%. In terms of upper limits, the supply gas hydrogen concentration can be less than 95%, e.g., less than 86.5%, less than 78%, less than 69.5%, less than 61%, less than 52.5%, less than 44%, less than 35.5%, less than 27%, or less than 18.5%. In terms of lower limits, the supply gas hydrogen concentration can be greater than 10%, e.g., greater than 18.5%, greater than 27%, greater than 35.5%, greater than 44%, greater than 52.5%, greater than 61%, greater than 69.5%, greater than 78%, or greater than 86.5%. Higher hydrogen concentrations, e.g., greater than 95%, and lower hydrogen concentrations, e.g., less than 10%, are also contemplated.

The concentrations of various components of the supply gas can be selected to support, improve, or optimize the functioning of metabolic networks within the organism. In certain aspects, the synthesis of the one or more biosynthetic products can involve a network of chemical reactions carried out by the organism of the culture. These reactions can combined have particular stoichiometric requirements for substrates used to synthesize the one or more products. For example, the synthesis can have a stoichiometric hydrogen requirement, a stoichiometric oxygen requirement, and/or a stoichiometric carbon dioxide requirement. In some embodiments, one or more ratios of the concentrations of substrates such as hydrogen, oxygen, and carbon dioxide within the culture are substantially identical to the ratios of the stoichiometric requirements of these substrates. In some embodiments, one or more ratios of the concentrations of substrates within the culture are greater than the ratios of stoichiometric requirements of these substrates. In such embodiments, one or more substrates can be provided in excess to the synthesis reactions such that these excess substrates are not limiting to the reactions.

The concentrations of gas-phase substrates within the liquid culture can depend in part on the solubility of these substrates within the liquid phase. These solubilities can be described by Henry's law, relating the amount of a dissolved gas to its partial pressure in the gas phase. The Henry's law relationship is a proportional one, with the proportionality constant for a chemical referred to as the Henry's law solubility constant of that chemical. Thus, the concentration of a substrate in the liquid culture will depend on the concentration of the substrate in the gas supply or gas feed and the Henry's law solubility constant of the substrate in the culture. In certain aspects in which hydrogen is not limiting to the synthesis of the one or more biosynthetic products by the culture organism, the ratio of (1a) the concentration of hydrogen in the supply gas to (1b) the concentration of oxygen in the supply gas is greater than the product of (2) the ratio of (2a) the stoichiometric hydrogen requirement to (2b) the stoichiometric oxygen requirement and (3) the ratio of (3a) the Henry's law solubility constant of hydrogen in the culture to (3b) the Henry's law solubility constant of oxygen in the culture. Similarly, in certain aspects in which carbon dioxide is not limiting to the synthesis, the ratio of (1a) the concentration of carbon dioxide in the supply gas to (1b) the concentration of oxygen in the supply gas is greater than the product of (2) the ratio of (2a) the stoichiometric carbon dioxide requirement to (2b) the stoichiometric oxygen requirement and (3) the ratio of (3a) the Henry's law solubility constant of carbon dioxide in the culture to (3b) the Henry's law solubility constant of oxygen in the culture.

The flow rate of the supply gas can be chosen to provide necessary nutrients and substrates to the culture at a rate sufficient to support desired culture growth and/or productivity rates. The supply gas flow rate can also be selected to be adequate in sweeping the headspace of the bioreactor at a rate necessary to remove off-gas components that such as products of interest or compounds inhibitory to the culture and/or the biosynthesis of the desired product. In certain aspects, the supply gas flow rate is monitored and adjusted as needed during the culture growth and/or biosynthetic reaction to increase one or more of yields, productivities, selectivities, or specificities of the growth and/or reaction.

The supply gas flow rate can be, for example, from 0.5 standard liter/minute/(liter of culture) to 5 standard liter/minute/(liter of culture), e.g., from 0.5 standard liter/minute/(liter of culture) to 3.2 standard liter/minute/(liter of culture), from 0.95 standard liter/minute/(liter of culture) to 3.65 standard liter/minute/(liter of culture), from 1.4 standard liter/minute/(liter of culture) to 4.1 standard liter/minute/(liter of culture), from 1.85 standard liter/minute/(liter of culture) to 4.55 standard liter/minute/(liter of culture), or from 2.3 standard liter/minute/(liter of culture) to 5 standard liter/minute/(liter of culture). In terms of upper limits, the supply gas flow rate can be less than 5 standard liter/minute/(liter of culture), less than 4.55 standard liter/minute/(liter of culture), less than 4.1 standard liter/minute/(liter of culture), less than 3.65 standard liter/minute/(liter of culture), less than 3.2 standard liter/minute/(liter of culture), less than 2.75 standard liter/minute/(liter of culture), less than 2.3 standard liter/minute/(liter of culture), less than 1.85 standard liter/minute/(liter of culture), less than 1.4 standard liter/minute/(liter of culture), or less than 0.95 standard liter/minute/(liter of culture). In terms of lower limits, the supply gas flow rate can be greater than 0.5 standard liter/minute/(liter of culture), e.g., greater than 0.95 standard liter/minute/(liter of culture), greater than 1.4 standard liter/minute/(liter of culture), greater than 1.85 standard liter/minute/(liter of culture), greater than 2.3 standard liter/minute/(liter of culture), greater than 2.75 standard liter/minute/(liter of culture), greater than 3.2 standard liter/minute/(liter of culture), greater than 3.65 standard liter/minute/(liter of culture), greater than 4.1 standard liter/minute/(liter of culture), or greater than 4.55 standard liter/minute/(liter of culture). Higher flow rates, e.g., greater than 5 standard liter/minute/(liter of culture), and lower flow rates, e.g., less than 0.5 standard liter/minute/(liter of culture), are also contemplated.

The culture of the gas fermentation can act as a biocatalyst, converting one or more components, e.g. target components, of the supply gas into metabolites and/or products. These, along with unreacted components of the supply gas, can then be exhausted as an off-gas produced with the culture. The off-gas of the biosynthetic system can include one or more products of the culture. These gaseous products can, for example, include products of respiration associated with culture growth and maintenance. The gaseous products can include other volatile compounds that the culture organism generates, either natively or as a result of genetic engineering and modification. The off-gas can include one or more side products of the metabolic or biosynthetic reactions used by the organism to produce the one or more biosynthetic products of interest. In such cases, the production of the off-gas includes the biosynthesis of the one or more biosynthetic products. The off-gas can include one or more components of the supply gas that have not been entirely consumed by the culture or dissolved into the culture liquid medium. The off-gas can include, for example, hydrogen, carbon dioxide, oxygen, or a combination thereof.

In some embodiments, the off-gas includes hydrogen. In certain aspects, the hydrogen in the off-gas includes hydrogen of the supply gas not consumed by the culture. In general, the lower the hydrogen molar flow rate in the off-gas relative to that of the supply gas, the higher the consumption of the supply gas hydrogen by the culture. The molar flow rate of hydrogen in the off-gas can be, for example, from 20% to 60% of the molar flow rate of hydrogen in the supply gas, e.g., from 20% to 44%, from 24% to 48%, from 28% to 52%, from 32% to 56%, or from 36% to 60% of the molar flow rate of hydrogen in the supply gas. In terms of upper limits, the molar flow rate of hydrogen in the off-gas can be less than 60% of the molar flow rate of hydrogen in the supply gas, e.g., less than 56%, less than 52%, less than 48%, less than 44%, less than 40%, less than 36%, less than 32%, less than 28%, or less than 24% of the molar flow rate of hydrogen in the supply gas. In terms of lower limits, the molar flow rate of hydrogen in the off-gas can be greater than 20% of the molar flow rate of hydrogen in the supply gas, e.g., greater than 24%, greater than 28%, greater than 32%, greater than 36%, greater than 40%, greater than 44%, greater than 48%, greater than 52%, or greater than 56% of the molar flow rate of hydrogen in the supply gas. Higher off-gas hydrogen molar flow rate, e.g., greater than 60% of the supply gas hydrogen molar flow rate, and lower molar flow rates, e.g., less than 20% of the supply gas hydrogen molar flow rate, are also contemplated. In some embodiments, more than 50% of the hydrogen in the supply gas is converted by the culture and does not appear in the off-gas. In some embodiments, more than 90% of the hydrogen in the supply gas, e.g., more than 92%, more than 94%, more than 96%, or more than 98%, is converted by the culture.

In certain aspects, the operation of the method is such that the amount of oxygen in the off-gas provides the off-gas with an improved safety profile. For example, the amount of oxygen in the off-gas can be low enough to provide a reduced risk of off-gas flammability, combustibility, or reactivity. In some embodiments, the concentration of oxygen in the off-gas is less than the limiting oxygen concentration for the off-gas composition. The concentration (v/v) of oxygen in the off-gas can be, for example, less than 7%, e.g., less than 6%, less than 5%, less than 4%, or less than 3%.

The method can further include forming the recycle gas from at least a portion of the off-gas. In some embodiments, the forming of the recycle gas does not include separating the one or more target components from the off-gas. In some aspects, the target component is a material that is at least partially consumed by the culture, such that the molar flow rate of the target component in the off-gas is less than the molar flow rate of the target component in the supply gas. This lower molar flow rate of the target component in at least a portion the off-gas, e.g., the portion of the off-gas used to form the recycle gas, is measured, and an amount of a supplemental gas necessary to be added the off-gas to form the recycle gas is calculated, wherein the supplemental gas has a determined concentration of the target component. The calculated amount of the supplemental gas is then combined with the portion of the off-gas to form the recycle gas, which is added as described above to the culture as part of the gas supply. In certain aspects, the recycle gas and the calculated amounts of each of the target components are combined to form the supply gas having concentrations of the target components within their respective target concentration ranges. In certain aspects, the recycle gas and the calculated amounts of each of the target components are combined to form the supply gas having flow rates of the target components within their respective target flow rate ranges.

The combining of the recycle gas and the supplemental gas streams, e.g., the calculated amounts of the target components, can occur outside of the fermenter such that the combined gases are introduced to the culture as a single stream. The combining of the recycle gas and the supplemental gas streams can occur within the fermenter such that the gases are introduced to the culture as separate streams. The supplemental gas can include one, two, three, four, five, six, seven, eight, nine, ten, or more than ten supplemental gas streams. In some embodiments, at least one of the supplemental gas streams has a different composition and/or flow rate than the recycle gas and each of the other supplemental gas streams. In some embodiments, each of the supplemental gas streams has a different composition and/or flow rate than the recycle gas and each of the other supplemental gas streams. In some embodiments, at least one of the supplemental gas streams has a composition and/or flow rate substantially identical to, e.g., within 10% of, that of the recycle gas. The supplemental gas streams and the recycle gas can be introduced to the culture in the same location of the fermenter, or at two or more different locations.

The recycle gas of the supply gas includes a target component having a concentration within a selected target range. The target component of the recycle gas can be any component selected to be added to the supply gas of the biosynthetic system. The target component can be, for example, one of the nutrients and substrates provided to the culture in the supply gas. For example, the target component can be a nutrient required for growth of the organism of the culture. The target component can be a substrate or cofactor of one or more metabolic reactions of the organism leading to synthesis of the one or more biosynthetic products. In some embodiments, the target component is hydrogen, oxygen, or carbon dioxide. Because the culture generally consumes at least a portion of this target component, the concentration of the target component is typically lower in an off-gas produced by the culture than in the supply gas fed to the culture.

The measuring of the target component concentrations within the off-gas portion, e.g., the recycle gas, can be performed on an as needed basis, or at regular, e.g., timed, intervals. The measuring can involve any processes generally known for quantifying gas phase component concentrations. These processes can include, for example, spectrophotometry, fluorescence or chemiluminescence detection, chromatography, flame ionization, mass spectrometry, or spectroscopy.

In some embodiments, the concentrations and flow rates of the target components in the supplemental gas streams are calculated by first determining the molar flow rate in the supply gas of the target components (mmol/Liter of culture/hr) required for the process based on a desired total gas flow to the culture (standard liter of gas/Liter of culture/min). The total flow and concentration of the target components are measured in the off-gas, and the percentage of the off-gas that is to be recycled is determined. In certain aspects, based on the percentage of off-gas flow to be recycled, the total flow of off-gas, and the composition of the target components in the off-gas, calculate the molar flow of each of the target components in the recycled off-gas stream is calculated. In certain aspects, based on the molar flow of the target components in the feed gas and the expected flow of target components in the recycled off-gas stream, the molar flow of the target components in the make-up gas (feed gas plus supplemental gas) is calculated. In certain aspects, based on the preferred allocation of gas flows between the feed gas and the supplemental gas, the molar flow of each target component in the feed and supplemental gas is calculated. In some embodiments, the feed gas flow can be from 0 to 75% of the total supply gas feed. In other embodiments, the supplemental gas flow can be from 0 to 75% of the total supply gas feed.

The supplemental gas can have a predetermined concentration of the target component, or the concentration of each of the one or more target components within the supplement gas can be evaluated, e.g., calculated, according the measurement techniques described above. In certain aspects, the supplemental gas has a composition that is substantially identical to that of the supply gas. In other words, the concentration (v/v) of each component of the supplemental gas differs from the concentration (v/v) of the same component in the supply gas by less than a 10% absolute difference, e.g., less than 9%, less than 8%, less than 7%, less than 6%, less than 5%, less than 4%, less than 3%, less than 2%, or less than 1%. As used herein, the term "absolute difference" refers to the absolute value of the component percent concentration in one gas stream minus the component percent concentration in the other gas stream. For example, if the supply gas is composed of 2% (v/v) component A, and the supplemental gas is composed of 10% (v/v), then the absolute difference between these percent concentrations is 8% (10% minus 2%). This is in contrast to the relative difference between the percent concentrations, which is 5, or 500% (10% divided by 2%). In certain aspects, the supplemental gas has a composition that is substantially different from that of the supply gas. In other words, the supplemental gas can have at least one component with a concentration (v/v) that differs from the concentration (v/v) of the same component in the supply gas by greater than a 10% absolute difference, e.g., greater than 15%, greater than 20%, greater than 25%. greater than 30%, greater than 35%, greater than 40%, greater than 45%, or greater than 50%.

In certain embodiments, all of the off-gas is combined with the supplemental gas to form the recycle gas. In some embodiments, a portion of the off-gas is combined with the supplemental gas to form the recycle gas, and the off-gas not combined with the supplemental gas is a purge gas. The purge gas can be vented or otherwise released from the system, or can be treated to any desired further downstream processing steps. These steps can include, for example, one or more scrubbing steps, incineration steps, condensation steps, product removal steps, steps involving joining with one or more other gas streams, or combinations thereof.

The portion (v/v) of the off-gas, e.g., the recycle gas, combined with the supplemental gas can, for example, be any off-gas fraction between 0.1% and 99.9%. In some embodiments, the portion of the off-gas combined with the supplemental gas is from 0.1% to 50%, e.g., from 0.1% to 30%, from 5% to 35%, from 10% to 40%, from 15% to 45%, or from 20% to 50%. In some embodiments, the portion of the off-gas combined with the supplemental gas ranges from 50% to 99.9%, e.g., from 50% to 80%, from 55% to 85%, from 60% to 90%, from 65% to 95%, or from 70% to 99.9%. In terms of upper limits, the portion of the gas combined with the supplemental gas can be less than 99.9%, e.g., less than 99.8%, less than 99.7%, less than 99.4%, less than 99%, less than 98%, less than 96%, less than 92%, less than 86%, less than 73%, less than 50%, less than 27%, less than 14%, less than 8%, less than 4%, less than 2%, less than 1%, less than 0.6%, less than 0.3%, or less than 0.2%. In terms of lower limits, the portion of the off-gas combined with the supplemental gas can be greater than 0.1%, e.g., greater than 0.2%, greater than 0.3%, greater than 0.6%, greater than 1%, greater than 2%, greater than 4%, greater than 8%, greater than 14%, greater than 27%, greater than 50%, greater than 73%, greater than 86%, greater than 92%, greater than 96%, greater than 98% greater than 99%, greater than 99.4%, greater than 99.7%, or greater than 99.8%.

In some embodiments, the supply gas consists of a feed gas and the recycle gas. In some embodiments, the supply gas comprises the feed gas, the recycle gas, and one or more other gas streams such as make-up gases. These make-up gases can be used to supply the culture with one or more gas components not present in the feed gas or the recycle gas, or can be used to add more to the culture of a gas component that is already present in one or both of the feed gas and the recycle gas. In certain aspects, the one or more make-up gases each primarily, or substantially completely, consist of a single gas compound.

For example, the supply gas can include an oxygen make-up gas used to supply oxygen to the culture of organisms. In certain aspects, an oxygen make-up gas of the supply gas includes oxygen, and the feed gas of the supply gas includes hydrogen and is substantially free of oxygen. In this way, the hydrogen and oxygen of the supply gas can be kept separate from one another prior to addition to the bioreactor and/or culture, thereby reducing the risk of flammability or explosion. The oxygen make-up gas can primarily consist of oxygen, e.g. its oxygen concentration (v/v) can be greater than 50%, greater than 55%, greater than 60%, greater than 65%, greater than 70%, greater than 75%, greater than 80%, or greater than 85%. The oxygen make-up gas can substantially completely consist of oxygen, e.g., its oxygen concentration (v/v) can be greater than 90%, greater than 91%, greater than 92%, greater than 93%, greater than 94%, greater than 95%, greater than 96%, greater than 97%, greater than 98%, or greater than 99%.

In some embodiments, the supply gas includes a hydrogen make-up gas used to supply hydrogen to the culture of organisms. In certain aspects, a hydrogen make-up gas of the supply gas includes hydrogen, and the feed gas of the supply gas includes oxygen and is substantially free of hydrogen. In this way, the oxygen and hydrogen of the supply gas can be kept separate from one another prior to addition to the bioreactor and/or culture, thereby reducing the risk of flammability or explosion. The hydrogen make-up gas can primarily consist of hydrogen, e.g. its hydrogen concentration (v/v) can be greater than 50%, greater than 55%, greater than 60%, greater than 65%, greater than 70%, greater than 75%, greater than 80%, or greater than 85%. The hydrogen make-up gas can substantially completely consist of hydrogen, e.g., its hydrogen concentration (v/v) can be greater than 90%, greater than 91%, greater than 92%, greater than 93%, greater than 94%, greater than 95%, greater than 96%, greater than 97%, greater than 98%, or greater than 99%.

The organism used in the bioreactor or fermentation process can be a wild type organism or can be a genetically modified organism. The organism can have modifications to its genome, and/or the organism can be transformed with one or more vectors or plasmids. The organism can have modifications from being subjected to random mutagenesis, natural selection, or other means. In some embodiments, the organism has upregulated or downregulated expression of one or more enzymes as a result of genetic modification. In some embodiments, the organism expresses one or more exogenous enzymes as a result of genetic modification. In some embodiments, one or more enzymes of the organism have altered substrate selectivities and/or product specificities as a result of genetic modification. The organism can be selected or designed for compatibility with one or more operation characteristics of the bioreactor, e.g., agitation rate, aeration, pressure, shear, temperature, or pH. The organism can be a wild-type organism, an organism derived from directed evolution, or a genetically engineered, e.g., genetically modified, organism.

The organism can be an aerobe or an anaerobe. The organism can be a heterotroph or an autotroph. In certain aspects, the organism is a chemoautotroph. In some cases, the microorganism can be a variety of an aerobic organism. In certain aspects, the microorganism is *Cupriavidus necator* (*C. necator*) or an organism with properties similar thereto. *C. necator* (previously called *Hydrogenomonas eutrophus*, *Alcaligenes eutropha*, *Ralstonia eutropha*, and *Wautersia eutropha*) is a gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. A non-limiting example of a *C. necator* organism useful in the present disclosure is a *C. necator* of the H16 strain. In one non-limiting embodiment, a *C. necator* host of the H16 strain with at least a portion of the phaC1AB1 gene locus knocked out (ΔphaCAB), as described in U.S. patent application Ser. No. 15/717,216, teachings of which are incorporated herein by reference, is used. In some cases, the microorganism is selected from non-pathogenic members of the genera *Ralstonia*, *Wausteria*, *Cupriavidus*, *Alcaligenes*, *Burkholderia* or *Pandoraea*.

In some embodiments, the organism is a prokaryote. For example, the prokaryote can be from the bacterial genus *Escherichia* such as *Escherichia coli*; from the bacterial genus *Clostridia*, such as *Clostridium ljungdahlii*, *Clostridium autoethanogenum* or *Clostridium kluyveri*; from the bacterial genus *Corynebacteria*, such as *Corynebacterium glutamicum*; from the bacterial genus *Cupriavidus*, such as *Cupriavidus necator* or *Cupriavidus metallidurans*; from the bacterial genus *Pseudomonas*, such as *Pseudomonas fluorescens*, *Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus*, such as *Lactobacillus delbrueckii*; or from the bacterial genus *Lactococcus*, such as *Lactococcus lactis*.

In some embodiments, the host microorganism is a eukaryote, e.g., a fungus such as a yeast. For example, the eukaryote can be from the fungus genus *Aspergillus* such as *Aspergillus niger*; from the yeast genus *Saccharomyces*, such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia*, such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*.

The culture of the organism can have a concentration in terms of dry cell weight within the liquid culture medium that is, for example, from 5 g/L to 10 g/L, e.g., from 5 g/L to 8 g/L, from 6 g/L to 9 g/L, or from 7 g/L to 10 g/L. The culture can have a concentration from 10 g/L to 100 g/L, e.g., from 10 g/L to 64 g/L, from 19 g/L to 73 g/L, from 28 g/L to 82 g/L, from 37 g/L to 91 g/L, or from 46 g/L to 100 g/L. In terms of upper limits, the culture concentration can be less than 100 g/L, e.g., less than 91 g/L, less than 82 g/L, less than 73 g/L, less than 64 g/L, less than 55 g/L, less than 46 g/L, less than 37 g/L, less than 28 g/L, or less than 19 g/L. In terms of upper limits, the culture concentration can be greater than 10 g/L, e.g., greater than 19 g/L, greater than 28 g/L, greater than 37 g/L, greater than 46 g/L, greater than 55 g/L, greater than 64 g/L, greater than 73 g/L, greater than 82 g/L, or greater than 91 g/L. Higher concentrations, e.g., greater than 100 g/L, and lower concentrations, e.g., less than 5 g/L, are also contemplated.

The culture of the biosynthesis system can be within a bioreactor, e.g., a vessel configured for carrying out biological processes involving organisms or biochemically active substances derived from such organisms. These biological processes include, but are not limited to, culture growth and/or metabolism; biocatalytic reactions involving whole cells, cell lysates, or isolated enzymes; and fermentations. Bioreactors can be used with aerobic or anaerobic processes, and can operate in batch, fed batch, continuous, or semi-continuous modes. The bioreactor can include an agitation system, or can be not actively stirred. In some embodiments, the bioreactor is a loop reactor, through which material can be flowed in a continuous or semi-continuous process. In some embodiments, the bioreactor is a chemostat. The bioreactor can be selected from among any known bioreactor type and configuration, including single fermenters, multiple fermenters in series, stirred-tank fermenters, membrane fermenters, fixed-bed fermenters, fluidized-bed fermenters, single autoclaves, multiple autoclaves in series, plug flow fermenters, pneumatically agitated fermenters such as gas(air)-lift fermenters, with either internal draft tube loop or external loop, gas-lift fermenters with external loop having forced-circulation, bubble-column fermenters, fixed (packed) bed column fermenters, horizontal single fermenters with multiple compartments, and multistage column fermenters.

The bioreactor can include one or more sensors configured to measure one more parameters of the environment and/or culture within the bioreactor. The sensors can, for example, include one or more temperature sensors, pH sensors, pressure sensors, dissolved oxygen sensors, foaming sensors, optical density sensors, and other enzymatic, near-infrared, or mid-infrared sensors. The operating conditions of the bioreactor can be adjusted or maintained as needed to carry out processes within the bioreactor, and in some aspects the adjusting or maintaining involves measurements from the one or more sensors.

In some embodiments, the gauge pressure of the bioreactor is maintained within a desired range to influence factors such as gas solubility within the bioreactor. The gauge pressure within the bioreactor can be, for example, from 1 bar to 10 bar, e.g., from 1 bar to 6.4 bar, from 1.9 bar to 7.3 bar, from 2.8 bar to 8.2 bar, from 3.7 bar to 9.1 bar, or from 4.6 bar to 10 bar. In terms of upper limits, the bioreactor gauge pressure can be less than 10 bar, e.g., less than 9.1 bar, less than 8.2 bar, less than 7.3 bar, less than 6.4 bar, less than 5.5 bar, less than 4.6 bar, less than 3.7 bar, less than 2.8 bar, or less than 1.9 bar. In terms of lower limits, the bioreactor gauge pressure can be greater than 1 bar, e.g., greater than 1.9 bar, greater than 2.8 bar, greater than 3.7 bar, greater than 4.6 bar, greater than 5.5 bar, greater than 6.4 bar, greater than 7.3 bar, greater than 8.2 bar, or greater than 9.1 bar. Higher gauge pressures, e.g. greater than 10 bar, and lower gauge pressures, e.g., less than 1 bar, are also contemplated.

The one or more biosynthetic products can include a natural product of the culture organism. For example, the one or more products can include a primary metabolite or a secondary metabolite. The one or more products can include the product of a biocatalytic reaction carried out by the culture organism. The one or more products can include whole cells of the culture organism or components of such cells. In certain aspects, the products include one or more organic acids, alcohols, olefins, fatty acids, amino acids, alkanes, amines, or combinations thereof. In some embodiments, the one or more biosynthetic products include a poly(hydroxyalkanoate), e.g., poly(3-hydroxybutyrate). In some embodiments, the one or more biosynthetic products include single-cell protein.

In certain aspects, at least one of the one or more biosynthetic products is collected. The collection of at least one product can involve any one or more downstream processes generally known to be suitable for the at least partial separation and/or isolation of material from a reaction or bioprocess. The collection can, for example, involve centrifugations, cell disruptions, concentrations, precipitations, extractions, filtrations, crystallizations, distillations, chemical conversions, or combinations thereof. One or more biosynthetic products can be collected from the liquid or solid phase of the culture, or from the gas phase present in the headspace of a bioreactor or the off-gas.

As described above, oxygen is needed for the aerobic biosynthesis to occur and is introduced to the fermenter via a feed stream. In order to introduce gaseous feed streams into the fermenter in a safe manner, at least two different continuous streams of feeds can be used. At least one continuous stream comprises a flammable gas (e.g., hydrogen) and at least one feed stream comprises gaseous oxygen. The at least one feed stream comprising a flammable gas may optionally comprise oxygen at a concentration below the limiting oxygen concentration (LOC) for flammability and may optionally comprise all or a portion of the $CO_2$ gas feed. The at least one continuous stream comprising oxygen may comprise at least 15 wt. % oxygen and may be an air feed stream, an oxygen-enriched air stream, or a pure oxygen stream. Such a feed stream would not contain hydrogen gas but may optionally comprise all or a portion of the $CO_2$ gas feed. Each gas feed stream is introduced into the fermenter by means described elsewhere herein. By separating the hydrogen and a large portion of the oxygen into separate feed streams, a flammable gas mixture cannot form in the feed system and gas mixtures containing both hydrogen and oxygen are present only in the small-volume gas bubbles within the fermentation broth and within the headspace and effluent gas stream. In some aspects, the gaseous oxygen concentration in the dispersed gas phase bubbles within the broth may be at an increased value as compared to the gaseous oxygen concentration in the bulk gas phase, e.g., the headspace.

For aerobic reactions, air can be used as the source of oxygen. Alternatively or additionally, oxygen-enriched air or pure oxygen can be used, for example as an oxygen make-up gas. It can be preferable to operate an aerobic reaction at high oxygen concentration in the dispersed gas phase within a bioreactor to increase oxygen mass transfer and thereby improve productivity. This is because the rate of oxygen mass transfer from the gas phase to the liquid phase is often the rate-limiting step for aerobic microbial biosynthetic reactions. In certain aspects, because an oxygen make-up gas is physically separate from a feed gas stream comprising hydrogen, the amount of oxygen in the supply gas can be selected to have an overall oxygen concentration greater than the limiting oxygen concentration. In this way, higher oxygen amounts can be introduced into the bioreactor without increasing risk of supply gas flammability, combustibility, or reactivity. For example, in some embodiments, the feed gas comprises hydrogen and the oxygen make-up gas comprises an oxygen concentration (v/v) that is greater than 3%, e.g., greater than 4%, greater than 5%, greater than 6%, greater than 7%, greater than 8%, greater than 9%, greater than 10%, greater than 12%, greater than 14%, greater than 16%, greater than 18%, or greater than 20%.

In order to maintain the DO and LOC within the desired ranges, there may be two or more oxygen addition points, e.g., three or more, four or more, five or more, or six or more. As more oxygen addition points are included in the fermenter, the more constant the DO concentration may be throughout the fermentation liquid. For example, in a vertical column fermenter, such as a gas-lift fermenter, the DO concentration may be maintained vertically. As more oxygen addition points are added, however, the complexity and cost of the reactor design increases.

The oxygen addition points to the fermenter need not be linearly spaced and may be spaced on more than one side of the fermenter. The feed stream comprising oxygen may be delivered by a pipe that extends through the fermenter wall and terminates with some type of gas distribution device as described herein, e.g., a sparger. This allows for the feed stream to be distributed across the fermenter diameter.

Assuming a vertical fermenter, the feed stream comprising oxygen may be added at the bottom of the fermenter. In some aspects, the feed stream is air, oxygen-enriched air, or pure oxygen. The oxygen concentration may therefore be greater at the bottom of the fermenter than at the top of the fermenter. Oxygen addition points above the initial feed stream comprising oxygen allow for the DO concentration to be controlled to be more uniform throughout the fermentation liquid. In some embodiments, the feed stream that is free of gaseous oxygen may be introduced at the bottom of the fermenter and the feed stream comprising oxygen may be added above this point. Further oxygen addition points up the column in combination with adding the feed stream free of gaseous oxygen allows for more uniform DO through the fermentation liquid. The feed stream that is free of oxygen includes a flammable component, e.g., hydrogen or combinations of carbon dioxide and hydrogen. The mass transfer rate may be staged along the length of the column (whether vertical or horizontal), and oxygen addition points may be chosen accordingly.

The oxygen may be added gradually, along multiple oxygen injection points, e.g., multiple microbubble generation modules, along the length of the fermenter. This set-up allows for gradual oxygen addition which improves the ability to operate below the LOC, though it is balanced with the oxygen mass transfer rate. The oxygen addition to each module may be individually controlled based on measurements of the DO concentration.

In some embodiments, the upper limit for gaseous oxygen concentration in the headspace of the fermenter is limited by safety considerations. Typically, the literature quotes a ratio of 7:1:1 or 8:1:1 for $H_2/CO_2/O_2$ (hydrogen/carbon dioxide/oxygen) for the initial gas mixture for optimum growth/production conditions for gas fermentation for *C. necator* (Ishizaki et al 2001), although this ratio may vary depending on adjustments and reaction needs. Generally, however, this means that the hydrogen/oxygen ratio is within the flammable range for hydrogen and oxygen gas concentrations. The critical oxygen concentration when mixed with hydrogen with carbon dioxide as a diluent is 5.9 vol % (Jones and Kenny, 1935). Therefore, the LOC of 5.9 vol % is here defined to be the minimum oxygen concentration at which a flammable gaseous mixture may form with gas fermentation process mixtures according to the present disclosure. These gas fermentation process mixtures are those which result in an oxygen, nitrogen, hydrogen, carbon dioxide and water vapour mixture in the headspace of the fermenter. Temperature and pressure conditions in the fermenter may also influence the relative concentration of components in the headspace. The fermenter is therefore operated below the LOC of 5.9 vol % oxygen. In order to maintain a safety margin, the fermenter may be operated within 70% to 80% of the LOC, or even less than 70%. In some aspects, the gaseous oxygen concentration in the headspace is controlled to be from 3.5 to 4.5 vol. % oxygen, e.g., from 3.75 to 4.25 vol. %, from 3.85 to 4.15 vol. %, from 3.95 to 4.05 vol. %, or approximately 4 vol. % oxygen. The fermenter effluent gas also has the same LOC.

In further aspects, the present disclosure is also directed to measuring and controlling the gaseous oxygen concentration in the headspace of the fermenter in which the aerobic biosynthesis occurs. This gaseous oxygen concentration in the headspace can be controlled to be less than the limiting oxygen concentration (LOC) for flammability of the gaseous mixture in the headspace, e.g., less than 85% of the LOC. In some embodiments, the reactor system interacts with at least one control loop configured to measure and control dissolved oxygen concentration in the fermentation liquid. The reactor system interact with an additional control loop to measure and control gaseous oxygen concentration in the headspace of the fermenter. The control loops can use feed forward controls, feedback controls, and combinations thereof.

Figure 3:
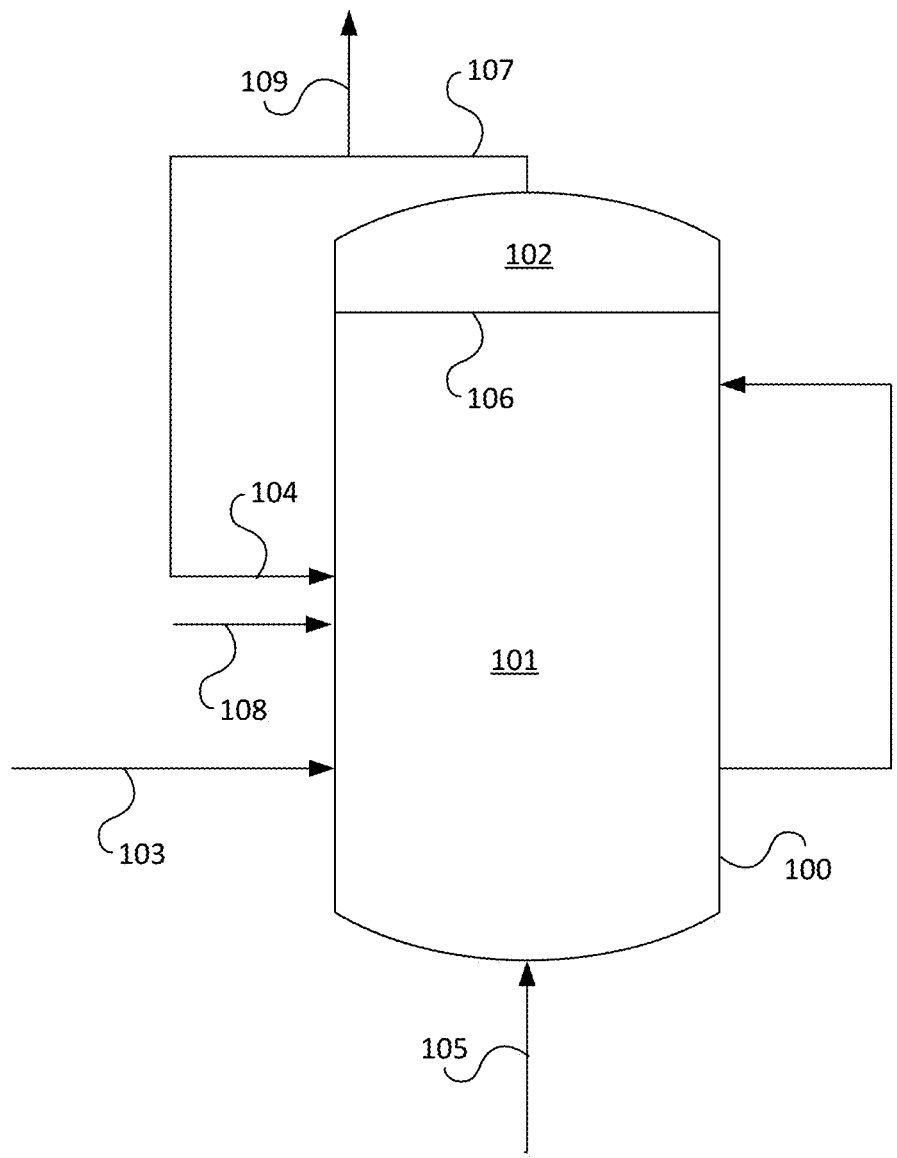
FIG. 3 is a schematic illustration of a reactor system suitable for use with a provided embodiment.
Figure 4:
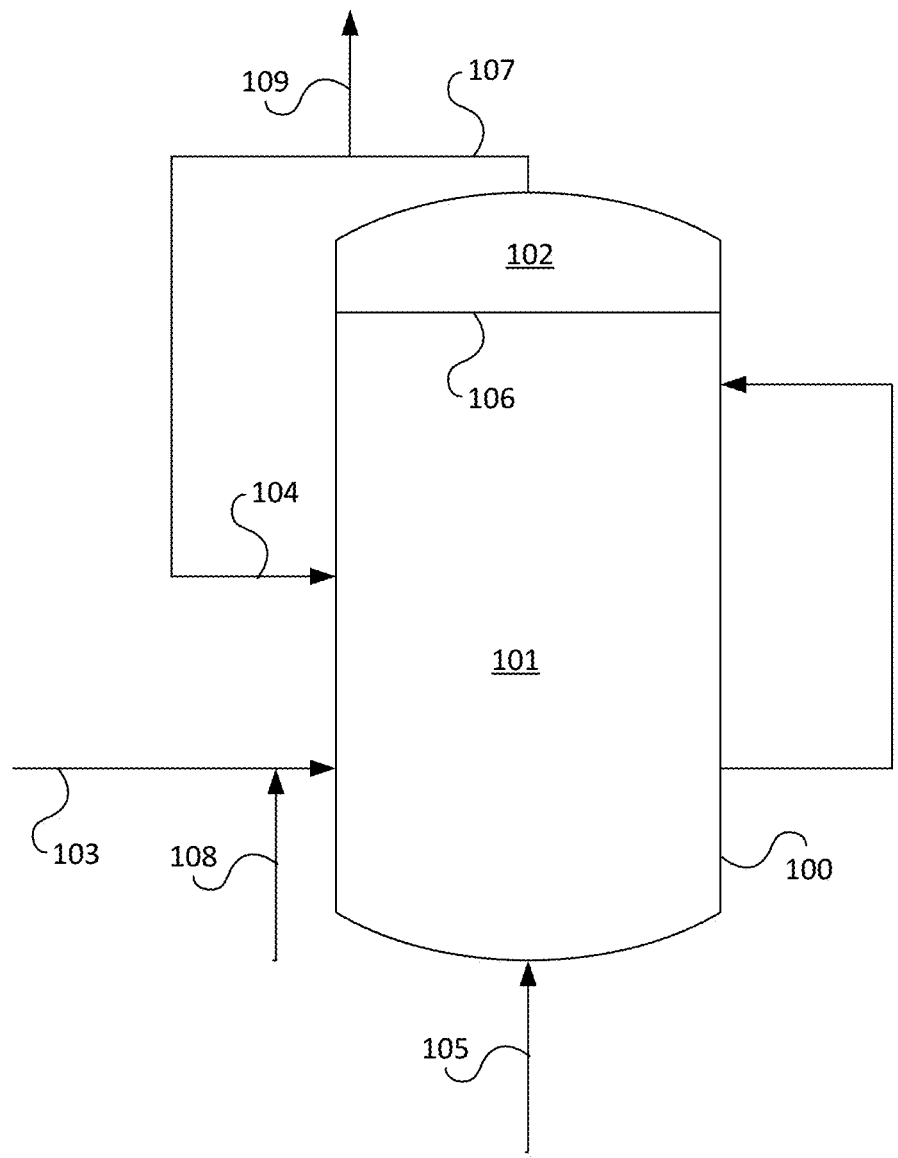
FIG. 4 is a schematic illustration of a reactor system suitable for use with a provided embodiment.
Figure 5:
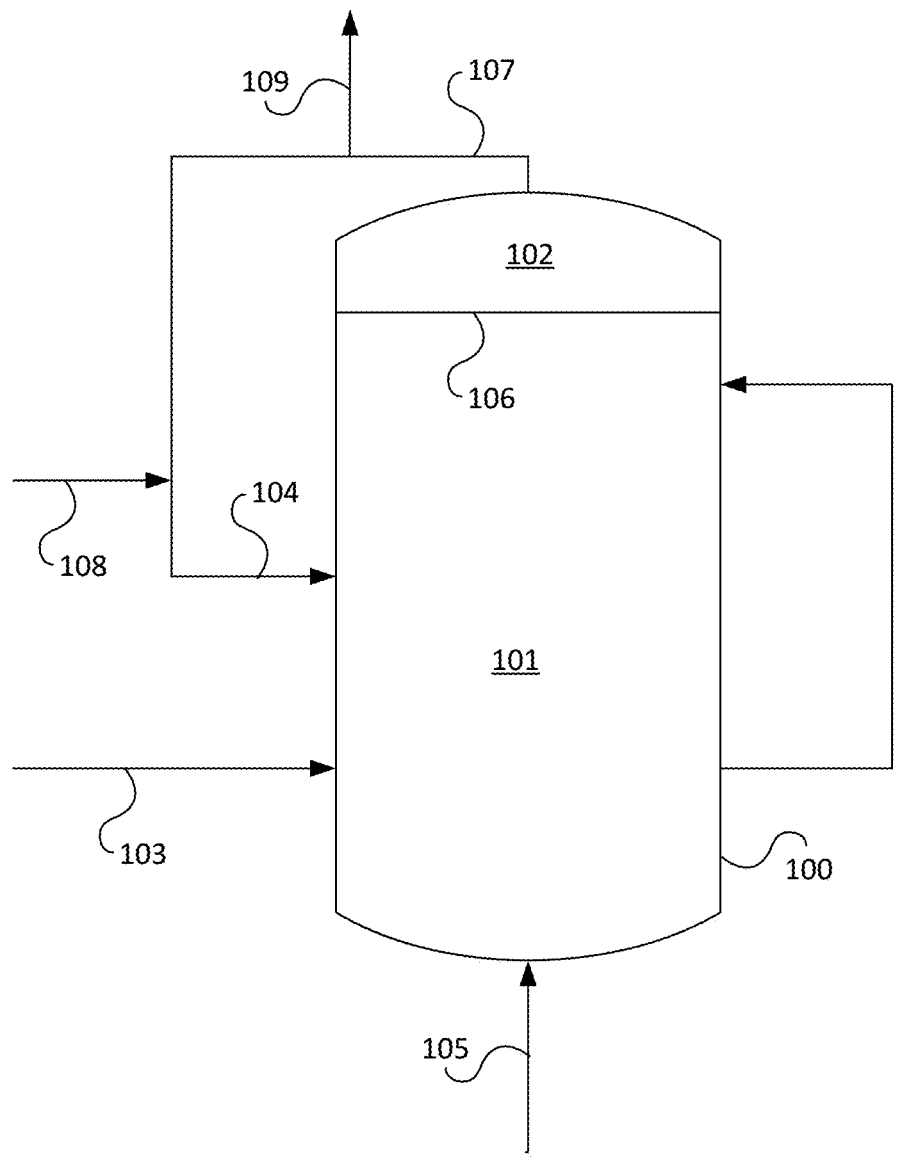
FIG. 5 is a schematic illustration of a reactor system suitable for use with a provided embodiment.

FIGS. 3-5 illustrate an exemplary system suitable for use with the disclosed method. The system of FIGS. 3-5 includes a bioreactor 100 containing a liquid culture 101 and a gas headspace 102. The bioreactor is fed with a supply gas that comprises a feed gas 103 and a recycle gas 104. The supply gas of FIGS. 3-5 also includes an optional make-up gas 105, e.g., an oxygen make-up gas. The supply gas is introduced to the culture through separate input ports, each of which are below the gas-liquid surface 106 of the culture. Because each stream of the supply gas is separate, the feed gas can include a high concentration of hydrogen and little to no oxygen, and the make-up gas can include a high concentration of oxygen and little to no hydrogen. In this way, the oxygen concentration within each individual gas stream is maintained below the limiting oxygen concentration, while the overall amount of oxygen in the total supply gas is greater than the limiting oxygen concentration were the oxygen present in the same stream as the overall amount of hydrogen in the total gas supply.

Also shown in FIGS. 3-5 is the off-gas 107 exiting the headspace 102 of the bioreactor 100. At least a portion of the off-gas can be produced by the culture during the biosynthesis by the culture of one or more desired bioproducts. The concentrations of one or more target components, e.g., hydrogen, oxygen, and/or carbon dioxide, within a portion of the off-gas is measured, and the amount of supplemental gas 108 to be added to the system is calculated. In the system of FIG. 5, the supplemental gas 108 is added to the off-gas portion 107 to form the recycle gas 104. The off-gas portion and the calculated amount of supplemental gas are combined, and the portion of the off-gas not combined with the supplemental gas exits the illustrated section of the system as a purge gas 109. In the system of FIG. 4, the supplemental gas 108 is added to the feed gas 103. In the system of FIG. 3, the supplemental gas 108 is added directly to the culture as a separate stream of the supply gas.

The present subject matter is well adapted to attain the ends and advantages mentioned as well as those that are inherent therein. The particular embodiments disclosed above are illustrative only, as the present subject matter can be modified and practiced in different but equivalent manners apparent to those skilled in the art having the benefit of the teachings herein. Furthermore, no limitations are intended to the details of construction or design herein shown, other than as described in the claims below. While compositions and methods are described in terms of "comprising," "containing," or "including" various components or steps, the compositions and methods can also "consist essentially of" consist of the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that can be incorporated herein by reference, the definitions that are consistent with this specification should be adopted.

The following examples are provided by way of illustration only and not by way of limitation. Those of skill in the art will readily recognize a variety of non-critical parameters that could be changed or modified to yield essentially the same or similar results.

EXAMPLES

A culture of *C. necator* H16 strain was grown in an 80-1 loop bioreactor maintained at a gauge pressure of 3.5 bar. The culture medium was a minimal medium broth that was pH controlled at pH 6.6, and foam controlled with the addition of TWEEN® 80 to maintain a 30% gas hold up. A feed gas of air supplemented with hydrogen at a concentration of 52% (v/v) and carbon dioxide at a concentration of 4% (v/v) was added to the bioreactor at a feed rate of 1.27 standard liter/minute. This level of hydrogen was in excess of that needed to support culture growth and maintenance and product biosynthesis. The oxygen concentration in the bioreactor headspace was maintained at less than 4% (v/v), and the oxygen uptake rate of the culture was maintained from 200 mM/hr to 230 mM/hr. The dissolved oxygen level of the culture was set to maintain oxygen limitation. Further data from this comparative example (Comparative Example A) are presented in Table 1 below. From the data it can be seen that in the single pass of the feed gas through the bioreactor, 34% of the hydrogen was consumed by the culture to produce additional biomass that includes 15-20 wt % intracellular poly(3-hydroxybutyrate) generated as a desired biosynthetic product.

TABLE 1

| Gas Fed Bioreactor Results | | | | | |
| --- | --- | --- | --- | --- | --- |
| | Comp. A | Comp. B | Comp. C | Ex. 1 | Ex. 2 |
| Total feed gas (std. liter/min/Liter) | 1.3 | 1.3 | 1.3 | 1.3 | 1.3 |
| Supply gas $H_2$ concentration (v/v) | 52% | 30% | 87% | 87% | 87% |
| Supply gas $CO_2$ concentration (v/v) | 4% | 4% | 4% | 4% | 4% |
| Supply gas $O_2$ concentration (v/v) | 9% | 9% | 9% | 9% | 9% |
| Supply gas $N_2$ concentration (v/v) | 34% | 57% | — | — | — |
| Total off-gas (std. liter/min/Liter) | 0.92 | 0.92 | 0.92 | 0.92 | 0.92 |
| Off-gas $H_2$ concentration (v/v) | 47% | 17% | 94% | 94% | 94% |
| Off-gas $CO_2$ concentration (v/v) | 2% | 42% | 42% | 42% | 42% |
| Off-gas $O_2$ concentration (v/v) | 4% | 4% | 4% | 4% | 4% |
| Off-gas $N_2$ concentration (v/v) | 48% | 77% | — | — | — |
| Make up gas (std. liter/min/Liter) | — | — | — | 0.384 | 0.384 |
| Make up gas $H_2$ concentration (v/v) | — | — | — | 65% | 65% |
| Make up gas $CO_2$ concentration (v/v) | — | — | — | 10% | 10% |
| Make up gas $O_2$ concentration (v/v) | — | — | — | 25% | 25% |
| Make up gas $N_2$ concentration (v/v) | — | — | — | — | — |
| Off-gas recycle | — | — | — | 100% | 95% |
| Biomass concentration (g/L) | 36 | 36 | 36 | 36 | 36 |
| Dilution rate ($hr^{-1}$) | 0.05 | 0.05 | 0.05 | 0.05 | 0.05 |
| Oxygen uptake rate (mM/hr) | 230 | 230 | 230 | 230 | 230 |
| Biomass production rate (g/L/hr) | 1.8 | 1.8 | 1.8 | 1.8 | 1.8 |
| Hydrogen conversion per pass | 34% | 60% | 34% | 21% | 21% |

TABLE 1-continued

Gas Fed Bioreactor Results

|  | Comp. A | Comp. B | Comp. C | Ex. 1 | Ex. 2 |
|---|---|---|---|---|---|
| Total hydrogen conversion rate | 34% | 60% | 34% | 100% | 85% |
| Hydrogen consumption ((liter $H_2$ )/(g biomass produced)) | 22.5 | 12.9 | 7.8 | 7.8 | 9.3 |

In a second comparative example (Comparative Example B), a culture of *C. necator* H16 strain was grown in the 80-1 loop bioreactor maintained at a gauge pressure of 3.5 bar. The culture medium was a minimal medium broth that was pH controlled at pH 6.6, and foam controlled with the addition of TWEEN® 80 to maintain a 30% gas hold up. A feed gas of air supplemented with hydrogen at a concentration of 30% (v/v) and carbon dioxide at a concentration of 4% (v/v) was added to the bioreactor at a feed rate of 1.27 standard liter/minute. This level of hydrogen was calculated to give a stoichiometric ratio of hydrogen to oxygen, as determined from observed hydrogen uptake rates and oxygen uptake rates of the culture. The feed gas also included nitrogen as a diluent. The oxygen concentration in the bioreactor headspace was maintained at less than 4% (v/v), and the oxygen uptake rate of the culture was maintained from 200 mM/hr to 230 mM/hr. The dissolved oxygen level of the culture was set to maintain oxygen limitation. Further data from this comparative example are presented in Table 1 above. From the data it can be seen that in the single pass of the feed gas through the bioreactor, 60% of the hydrogen was consumed by the culture to produce additional biomass that includes 15-20 wt % intracellular poly(3-hydroxybutyrate) generated as a desired biosynthetic product.

In a third comparative example (Comparative Example C), a culture of *C. necator* H16 strain was grown in the 80-1 loop bioreactor maintained at a gauge pressure of 3.5 bar. The culture medium was a minimal medium broth that was pH controlled at pH 6.6, and foam controlled with the addition of TWEEN® 80 to maintain a 30% gas hold up. A feed gas of hydrogen (87%) supplemented with oxygen at a concentration of 9% (v/v) and carbon dioxide at 4% (v/v) was added to the bioreactor at a feed rate of 1.27 standard liter/minute. This level of hydrogen was calculated to give a stoichiometric ratio of hydrogen to oxygen, as determined from observed hydrogen uptake rates and oxygen uptake rates of the culture. The feed gas also included nitrogen as a diluent. The oxygen concentration in the bioreactor headspace was maintained at less than 4% (v/v), and the oxygen uptake rate of the culture was maintained from 200 mM/hr to 230 mM/hr. The dissolved oxygen level of the culture was set to maintain oxygen limitation. Further data from this comparative example are presented in Table 1 above. From the data it can be seen that in the single pass of the feed gas through the bioreactor, 60% of the hydrogen was consumed by the culture to produce additional biomass that includes 15-20 wt % intracellular poly(3-hydroxybutyrate) generated as a desired biosynthetic product.

In a fourth comparative example, off-gas was recycled to the culture to improve the hydrogen gas conversion. In order to maintain the total supply gas flow at 1.3 standard liter/min/Liter of culture, and maintain the oxygen (from air feed) and carbon dioxide flow rates, no additional hydrogen make-up gas could be added to the feed or supplemental gas streams. The hydrogen concentration and flow in the supply feed dropped and a steady state growth or product production was not achievable with off-gas recycle without gas separation to reduce the nitrogen concentration.

A culture of *C. necator* H16 strain was then grown in the 80-1 loop bioreactor maintained at a gauge pressure of 3.5 bar and with a gas recycle as Example 1. The culture medium was a minimal medium broth that was pH controlled at pH 6.6, and foam controlled with the addition of TWEEN® 80 to maintain a 30% gas hold up. A supply gas of hydrogen at a concentration of 87% (v/v) supplemented with oxygen at a concentration of 9% (v/v) and carbon dioxide at a concentration of 4% (v/v) was added to the bioreactor, along with an oxygen make-up gas, to give a total supply gas feed rate of 1.27 standard liter/minute. The oxygen concentration in the bioreactor headspace was maintained at less than 4% (v/v), and the oxygen uptake rate of the culture was maintained from 200 mM/hr to 230 mM/hr. The dissolved oxygen level of the culture was set to maintain oxygen limitation. Substantially all of the off-gas was recycled to the bioreactor and feed gas and/or supplemental gas is combined with the recycled off-gas in the reactor to make up a constant supply gas of the specified gas component concentration. Further data from this example are presented in Table 1 above. From the data it can be seen that in repeated passes of the total supply gas through the bioreactor, substantially all of the hydrogen was consumed by the culture to produce additional biomass that includes 15-20 wt % intracellular poly(3-hydroxybutyrate). These results demonstrate that hydrogen conversion rates of high hydrogen utilizing biosynthetic processes can be significantly improved with the use of the provided gas recycling methods. The results also demonstrate that high oxygen concentrations and hydrogen concentrations can be added to such a bioprocess using the provided methods.

A culture of *C. necator* H16 strain was then grown in the 80-1 loop bioreactor maintained at a gauge pressure of 3.5 bar and with a gas recycle and gas purge as Example 2. The culture medium was a minimal medium broth that was pH controlled at pH 6.6, and foam controlled with the addition of TWEEN® 80 to maintain a 30% gas hold up. A supply gas of hydrogen at a concentration of 87% (v/v) supplemented with oxygen at a concentration of 9% (v/v) and carbon dioxide at a concentration of 4% (v/v) was added to the bioreactor, along with an oxygen make-up gas, to give a total supply gas feed rate of 1.27 standard liter/minute. The oxygen concentration in the bioreactor headspace was maintained at less than 4% (v/v), and the oxygen uptake rate of the culture was maintained from 200 mM/hr to 230 mM/hr. The dissolved oxygen level of the culture was set to maintain oxygen limitation. A portion of the off-gas equaling 95% (v/v) was recycled to the bioreactor, with the remaining 5% of the off-gas bled from the bioreactor in the form of a purge gas to prevent the build-up of non-reacting gas components. Further data from this example are presented in Table 1 above. From the data it can be seen that in repeated passes of the total supply gas through the bioreactor, 85% of the hydrogen was consumed by the culture to produce additional biomass that includes 15-20 wt % intracellular poly(3- hydroxybutyrate). These results demonstrate that the provided gas recycle methods provide advantages in hydrogen utilization even under conditions in which a portion of the off-gas is released as a purge and not added to the gas recycle.

Embodiments

The following embodiments are contemplated. All combinations of features and embodiment are contemplated.

Embodiment 1: A method for recycling an off-gas stream in a gas fermentation biosynthetic system, the method comprising: providing a culture of a chemoautotrophic organism capable of synthesis of one or more biosynthetic products to a gas fermentation reactor system; introducing a supply gas to the culture, wherein the supply gas comprises a recycle gas, wherein the concentration of nitrogen in the supply gas is less than 5% (v/v), wherein the concentrations of one or more target components in the supply gas are each independently within a target concentration range, and wherein the one or more target components are selected from the group consisting of hydrogen, carbon dioxide, and oxygen; producing, with the culture, an off-gas; forming the recycle gas from at least a portion of the off-gas; measuring the concentrations of each of the one or more target components in the recycle gas; calculating an amount of each of the one or more target components to be combined with the recycle gas to form the supply gas having concentrations of the one or more target components within the target concentration ranges; and introducing the recycle gas and the calculated amounts of each of the one or more target components to the culture.

Embodiment 2: An embodiment of embodiment 1, wherein the flow rates of the one or more target components in the supply gas are each independently within a target flow rate range; the method further comprises measuring the flow rates of each of the one or more target components in the recycle gas; and the calculating comprises calculating an amount of each of the one or more target components to be combined with the recycle gas to form the supply gas having concentrations of the one or more target components within the target concentration ranges and having flow rates of the one or more target components within the target flow rate ranges.

Embodiment 3: An embodiment of embodiment 1 or 2, wherein the one or more target components comprise hydrogen, carbon dioxide, and oxygen.

Embodiment 4: An embodiment of any of the embodiments of embodiment 1-3, wherein the forming of the recycle gas does not comprise separating the one or more target components from the off-gas.

Embodiment 5: An embodiment of any of the embodiments of embodiment 1-4 wherein the one or more target components comprise oxygen, and wherein the target concentration of oxygen is from 2% (v/v) to 20% (v/v).

Embodiment 6: An embodiment of any of the embodiments of embodiment 1-5, wherein the one or more target components comprise hydrogen, and wherein the target concentration of hydrogen is from 10% (v/v) to 95% (v/v).

Embodiment 7: An embodiment of any of the embodiments of embodiment 1-6, wherein the one or more target components comprise carbon dioxide, and wherein the target concentration of carbon dioxide is from 1% (v/v) to 50% (v/v).

Embodiment 8: An embodiment of any of the embodiments of embodiment 1-7, wherein the concentration of nitrogen in the supply gas is less than 1% (v/v).

Embodiment 9: An embodiment of any of the embodiments of embodiment 1-8, wherein the concentration of nitrogen in the supply gas is less than 0.1% (v/v).

Embodiment 10: An embodiment of any of the embodiments of embodiment 1-9, wherein the supply gas further comprises one or more supplemental gas streams, wherein the supplemental gas streams comprise the calculated amounts of the one or more target components, and wherein the supply gas has a flow rate from 0.5 standard liter/minute/(liter of culture) to 5 standard liter/minute/(liter of culture).

Embodiment 11: An embodiment of embodiment 10, wherein at least one of the one or more supplemental gas streams consists essentially of oxygen.

Embodiment 12: An embodiment of embodiment 10 or 11, wherein the one or more supplemental gas streams comprise two or more supplemental gas streams, wherein the concentrations and flow rates of the one or more target components in at least one of the two or more supplemental gas streams is different from the concentrations and flow rates of the one or more target components in each other of the two or more supplemental gas streams.

Embodiment 13: An embodiment of any of the embodiments of embodiment 10-12, wherein at least one of the one or more supplemental gas streams is combined with the recycle gas prior to introduction to the culture.

Embodiment 14: An embodiment of any of the embodiments of embodiment 10-13, wherein the flow rate and composition of the recycle gas are each different from the flow rate and composition of each of the one or more supplemental gas streams.

Embodiment 15: An embodiment of any of the embodiments of embodiment 10-13, wherein the flow rate and composition of the recycle gas are each within 10% of the flow rate and composition of at least one of the one or more supplemental gas streams.

Embodiment 16: An embodiment of any of the embodiments of embodiment 10-15, wherein the recycle gas and each of the one or more supplemental gas streams is non-flammable prior to introduction to the culture.

Embodiment 17: An embodiment of any of the embodiments of embodiment 10-16, wherein the oxygen concentration in the recycle gas and in each of the one or more supplemental gas streams is less than the limiting oxygen concentration (LOC), or wherein the hydrogen concentration in the recycle gas and in each of the one or more supplemental gas streams is below the lower flammability limit (LFL).

Embodiment 18: An embodiment of any of the embodiments of embodiment 10-17, wherein the gaseous oxygen concentration in the supply gas is higher than the LOC.

Embodiment 19: An embodiment of any of the embodiments of embodiment 1-18, wherein the supply gas is introduced into the culture as at least two supply gas streams, wherein at least one of the supply gas streams comprises gaseous oxygen and either no hydrogen or hydrogen at a concentration below the LFL, and wherein at least one other of the supply gas streams comprises hydrogen and either no oxygen or oxygen at a concentration below the LOC.

Embodiment 20: An embodiment of any of the embodiments of embodiment 1-19, further comprising: maintaining the gaseous oxygen concentration in a headspace of the gas fermentation reactor below the LOC by controlling the flow rate and composition of the supply gas.

Embodiment 21: An embodiment of embodiment 20, wherein the gaseous oxygen concentration in the headspace is maintained below 75% of the LOC.

Embodiment 22: An embodiment of any of the embodiments of embodiment 1-21, wherein the gas fermentation reactor system is selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 23: An embodiment of any of the embodiments of embodiment 1-22, wherein the gas fermentation reactor system is a chemostat.

Embodiment 24: An embodiment of any of the embodiments of embodiment 1-23, wherein the gas fermentation reactor system is not actively stirred.

Embodiment 25: An embodiment of any of the embodiments of embodiment 1-24, wherein the gas fermentation reactor system has a gauge pressure from 1 bar to 10 bar.

Embodiment 26: An embodiment of any of the embodiments of embodiment 1-25, wherein the recycle gas is formed from more than 50% (v/v) of the off-gas.

Embodiment 27: An embodiment of any of the embodiments of embodiment 1-26, wherein the portion of the off-gas not used to form the recycle gas is purged from the gas fermentation reactor.

Embodiment 28: An embodiment of any of the embodiments of embodiment 1-27, wherein more than 50% of the hydrogen in the supply gas is converted by the culture.

Embodiment 29: An embodiment of any of the embodiments of embodiment 1-28, wherein more than 90% of the hydrogen in the supply gas is converted by the culture.

Embodiment 30: An embodiment of any of the embodiments of embodiment 1-29, wherein the chemoautotrophic organism is selected from non-pathogenic members of the genera *Ralstonia, Wausteria, Cupriavidus, Alcaligenes, Burkholderia* or *Pandoraea*.

Embodiment 31: An embodiment of embodiment 30, wherein the chemoautotrophic organism is *Cupriavidus necator*.

Embodiment 32: An embodiment of any of the embodiments of embodiment 1-31, wherein the chemoautotrophic organism is a genetically modified organism.

Embodiment 33: An embodiment of any of the embodiments of embodiment 1-32, wherein the concentration of the culture is from 5 g/L to 100 g/L.

Embodiment 34: An embodiment of any of the embodiments of embodiment 1-33, wherein the one or more biosynthetic products comprise one or more extracellular products selected from the group consisting of organic acids, alcohols, olefins, fatty acids, amino acids, alkanes, and amines.

Embodiment 35: An embodiment of any of the embodiments of embodiment 1-34, wherein the one or more biosynthetic products comprise a poly(hydroxyalkanoate).

Embodiment 36: An embodiment of embodiment 35, wherein the one or more biosynthetic products comprise poly(3-hydroxybutyrate).

Embodiment 37: An embodiment of any of the embodiments of embodiment 1-33, wherein the one or more biosynthetic products comprise single-cell protein.

Embodiment 38: An embodiment of any of the embodiments of embodiment 1-37, further comprising: collecting at least a portion of the one or more biosynthetic products.

Embodiment 39: A reactor system for an aerobic gas fermentation process, the system comprising: a gas fermentation reactor comprising at least two oxygen addition points; a culture of a chemoautotrophic organism capable of synthesis of one or more biosynthetic products; a supply gas comprising a recycle gas, wherein the concentration of nitrogen in the supply gas is less than 5% (v/v), wherein the concentrations of one or more target components in the supply gas are each independently within a target concentration range, and wherein the one or more target components are selected from the group consisting of hydrogen, carbon dioxide, and oxygen; a first control loop configured to measure and control dissolved oxygen content in a fermentation liquid in the gas fermentation reactor; a second control loop configured to measure and control gaseous oxygen concentration in a headspace of the gas fermentation reactor; a recycle loop configured to recycle at least a portion of an off-gas stream to the culture; analytical equipment to measure the concentrations of each of the one or more target components in the recycle gas; and a third control loop configured to calculate an amount of each of the one or more target components to be combined with the recycle gas to form the supply gas having concentrations of the one or more target components within the target concentration ranges, wherein the third control loop is further configured to introduce the recycle gas and the calculated amounts of each of the one or more target components to the culture.

Embodiment 40: An embodiment of embodiment 39, wherein the flow rates of the one or more target components in the supply gas are each independently within a target flow rate range.

Embodiment 41: An embodiment of embodiment 39 or 40, wherein the one or more target components comprise hydrogen, carbon dioxide, and oxygen.

Embodiment 42: An embodiment of any of the embodiments of embodiment 39-41, wherein the supply gas further comprises one or more supplemental gas streams.

Embodiment 43: An embodiment of embodiment 42, wherein the recycle gas and each of the one or more supplemental gas streams are non-flammable prior to introduction to the culture.

Embodiment 44: An embodiment of any of the embodiments of embodiment 39-41, wherein the supply gas further comprises one or more supplemental gas streams, and wherein (i) the oxygen concentration in the recycle gas and in each of the one or more supplemental gas streams is less than the limiting oxygen concentration (LOC), or (ii) the hydrogen concentration in the recycle gas and in each of the one or more supplemental gas streams is below the lower flammability limit (LFL).

Embodiment 45: An embodiment of any of the embodiments of embodiment 39-44, wherein the supply gas is introduced into the culture as at least two supply gas streams, wherein at least one of the supply gas streams comprises gaseous oxygen and either no hydrogen or hydrogen at a concentration below the LFL, and wherein at least one other of the supply gas streams comprises hydrogen and either no oxygen or oxygen at a concentration below the LOC.

Embodiment 46: An embodiment of any of the embodiments of embodiment 39-45, wherein the gaseous oxygen concentration in the supply gas is higher than the LOC.

Embodiment 47: An embodiment of any of the embodiments of embodiment 39-46, wherein the gas fermentation reactor is selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 48: An embodiment of any of the embodiments of embodiment 38-46, wherein the gas fermentation reactor system has a gauge pressure from 1 bar to 10 bar.

Embodiment 49: An embodiment of any of the embodiments of embodiment 39-48, wherein the recycle gas is formed from more than 50% (v/v) of the off-gas.

Embodiment 50: An embodiment of any of the embodiments of embodiment 39-49, wherein the portion of the off-gas not used to form the recycle gas is purged from the gas fermentation reactor.

Embodiment 51: An embodiment of any of the embodiments of embodiment 39-50, wherein more than 50% of the hydrogen in the supply gas is converted by the culture.

Embodiment 52: An embodiment of any of the embodiments of embodiment 38-51, wherein the chemoautotrophic organism is selected from non-pathogenic members of the genera *Ralstonia, Wausteria, Cupriavidus, Alcaligenes, Burkholderia* or *Pandoraea*.

Embodiment 53: An embodiment of embodiment 52, wherein the chemoautotrophic organism is *Cupriavidus necator*.

Embodiment 54: An embodiment of any of the embodiments of embodiment 39-53, wherein the chemoautotrophic organism is a genetically modified organism.

Embodiment 55: An embodiment of any of the embodiments of embodiment 39-54, wherein the concentration of the culture is from 5 g/L to 100 g/L.

Embodiment 56: A method for making one or more biosynthetic products, the method comprising: providing a culture of a chemoautotrophic organism capable of synthesis of the one or more biosynthetic products to a gas fermentation reactor system; introducing a supply gas to the culture, wherein the supply gas comprises a recycle gas, wherein the concentration of nitrogen in the supply gas is less than 5% (v/v), wherein the concentrations of one or more target components in the supply gas are each independently within a target concentration range, and wherein the one or more target components are selected from the group consisting of hydrogen, carbon dioxide, and oxygen; producing, with the culture, an off-gas and the one or more biosynthetic products; forming the recycle gas from at least a portion of the off-gas; measuring the concentrations of each of the one or more target components in the recycle gas; calculating an amount of each of the one or more target components to be combined with the recycle gas to form the supply gas having concentrations of the one or more target components within the target concentration ranges; and introducing the recycle gas and the calculated amounts of each of the one or more target components to the culture.

Embodiment 57: A biosynthetic product made using an embodiment of any of the embodiments of embodiment 1-56.

While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the disclosure. All US patents and publications cited herein are incorporated by reference in their entirety.

We claim:

1. A method for recycling an off-gas stream in a gas fermentation biosynthetic system, the method comprising:
   introducing a supply gas to a culture of a chemoautotrophic organism in a gas fermentation reactor system, wherein the organism is capable of synthesis of one or more biosynthetic products, wherein the concentration of hydrogen in the supply gas is from 86.5% to 95% (v/v), the concentration of carbon dioxide in the supply gas is from 1% to 4% (v/v), the concentration of oxygen in the supply gas is greater than 7.4%, and the concentration of nitrogen in the supply gas is less than 5% (v/v), wherein the concentrations of one or more target components in the supply gas are each independently within a target concentration range, and wherein the one or more target components are selected from the group consisting of hydrogen, carbon dioxide, and oxygen;
   maintaining a gaseous oxygen concentration in a headspace of the gas fermentation reactor system at 3.5% to 4.5%;
   producing, with the culture, an off-gas;
   forming a recycle gas from at least a portion of the off-gas, wherein the recycle gas comprises at least 50% (v/v) of the off-gas produced with the culture;
   measuring the concentrations of each of the one or more target components in the recycle gas;
   calculating an amount of each of the one or more target components to be combined with the recycle gas to form the supply gas having concentrations of the one or more target components within the target concentration ranges; and
   introducing the recycle gas and one or more supplemental gas streams comprising the calculated amounts of each of the one or more target components to the culture, wherein at least one of the one or more supplemental gas streams has a hydrogen concentration that is greater than 50%, less than a hydrogen concentration of the supply gas, and has an absolute difference in hydrogen concentration from the supply gas of 10% or more;
   wherein the method has a total hydrogen conversion rate of 96% or more of the hydrogen in the supply gas.

2. The method of claim 1, wherein
   flow rates of the one or more target components in the supply gas are each independently within a target flow rate range;
   the method further comprises measuring the flow rates of each of the one or more target components in the recycle gas; and
   the calculating comprises calculating an amount of each of the one or more target components to be combined with the recycle gas to form the supply gas having concentrations of the one or more target components within the target concentration ranges and having flow rates of the one or more target components within the target flow rate ranges.

3. The method of claim 1, wherein the one or more target components comprise hydrogen, carbon dioxide, and oxygen.

4. The method of claim 1, wherein the forming of the recycle gas does not comprise separating the one or more target components from the off-gas.

5. The method of claim 1, wherein the supply gas has a flow rate from 0.5 standard liter/minute/(liter of culture) to 5 standard liter/minute/(liter of culture).

6. The method of claim 1, wherein at least one of the one or more supplemental gas streams is combined with the recycle gas prior to introduction to the culture.

7. The method of claim 1, wherein the recycle gas and each of the one or more supplemental gas streams is non-flammable prior to introduction to the culture.

8. The method of claim 1, wherein the supply gas is introduced into the culture as at least two supply gas streams, wherein at least one of the supply gas streams comprises gaseous oxygen and either no hydrogen or hydrogen at a concentration below a lower flammability limit (LFL), and wherein at least one other of the supply gas streams comprises hydrogen and either no oxygen or oxygen at a concentration below a limiting oxygen concentration (LOC).

9. The method of claim 1, wherein maintaining the gaseous oxygen concentration in the headspace of the gas fermentation reactor system comprises measuring the gaseous oxygen concentration in the headspace, controlling a composition of the supply gas, and controlling a flow rate of the supply gas to the gas fermentation reactor system.

10. The method of claim 1, wherein the recycle gas comprises more than 86% (v/v) of the off-gas produced by the culture.

11. The method of claim 1, wherein the portion of the off-gas not used to form the recycle gas is purged from the gas fermentation reactor.

12. The method of claim 1, wherein the chemoautotrophic organism is *Cupriavidus necator* or *Cupriavidus metalliduruns*.

13. The method of claim 1, wherein the one or more biosynthetic products comprise a poly(hydroxyalkanoate).

14. The method of claim 1, wherein:
the one or more target components comprise oxygen, and wherein the target concentration of oxygen is from 2% (v/v) to 20% (v/v), or
the one or more target components comprise hydrogen, and wherein the target concentration of hydrogen is from 10% (v/v) to 95% (v/v), or
a combination thereof.

15. The method of claim 1, wherein the concentration of nitrogen in the supply gas is less than 1% (v/v).

16. The method of claim 1, wherein the method has a total hydrogen conversion rate of 98% or more of the hydrogen in the supply gas.

17. The method of claim 1, wherein the concentration of the dry cell weight of the culture provided to the gas fermentation reactor system is from 5 g/L to 100 g/L.

18. The method of claim 1, wherein the chemoautotrophic organism is *Cupriavidus necator*.

19. The method of claim 1, wherein the one or more biosynthetic products comprise poly(3-hydroxybutyrate).

20. The method of claim 1, wherein the one or more biosynthetic products comprise a single-cell protein.

* * * * *